United States Patent
Pastan et al.

(10) Patent No.: US 11,390,683 B2
(45) Date of Patent: Jul. 19, 2022

(54) ANTI-MESOTHELIN POLYPEPTIDES AND PROTEINS

(71) Applicant: The United States of America, as represented by the Secretary, Department of Health and Human Services, Bethesda, MD (US)

(72) Inventors: Ira H. Pastan, Chevy Chase, MD (US); Masanori Onda, Germantown, MD (US); Tapan Bera, Frederick, MD (US); Mitchell Ho, Urbana, MD (US)

(73) Assignee: The United States of America, as represented by the Secretary, Department of Health and Human Services, Bethesda, MD (US)

(*) Notice: Subject to any disclaimer, the term of this patent is extended or adjusted under 35 U.S.C. 154(b) by 149 days.

(21) Appl. No.: 16/613,971

(22) PCT Filed: May 17, 2018

(86) PCT No.: PCT/US2018/033236
§ 371 (c)(1),
(2) Date: Nov. 15, 2019

(87) PCT Pub. No.: WO2018/213612
PCT Pub. Date: Nov. 22, 2018

(65) Prior Publication Data
US 2020/0247901 A1    Aug. 6, 2020

Related U.S. Application Data

(60) Provisional application No. 62/508,197, filed on May 18, 2017.

(51) Int. Cl.
| | | |
|---|---|---|
| *C07K 16/30* | (2006.01) | |
| *A61K 39/395* | (2006.01) | |
| *G01N 33/574* | (2006.01) | |
| *A61P 35/00* | (2006.01) | |
| *A61K 47/68* | (2017.01) | |
| *C12N 15/63* | (2006.01) | |
| *A61K 39/00* | (2006.01) | |

(52) U.S. Cl.
CPC .......... *C07K 16/30* (2013.01); *A61K 47/6829* (2017.08); *A61P 35/00* (2018.01); *G01N 33/574* (2013.01); *A61K 39/395* (2013.01); *A61K 2039/505* (2013.01); *C12N 15/63* (2013.01); *C12N 2800/00* (2013.01)

(58) Field of Classification Search
CPC ......................... C07K 16/30; C07K 2317/34
See application file for complete search history.

(56) References Cited

U.S. PATENT DOCUMENTS

| | | | |
|---|---|---|---|
| 4,892,827 A | 1/1990 | Pastan et al. | |
| 5,075,109 A | 12/1991 | Tice et al. | |
| 5,225,539 A | 7/1993 | Winter | |
| 5,512,658 A | 4/1996 | Pastan et al. | |
| 5,545,806 A | 8/1996 | Lonberg et al. | |
| 5,569,825 A | 10/1996 | Lonberg et al. | |
| 5,585,089 A | 12/1996 | Queen et al. | |
| 5,602,095 A | 2/1997 | Pastan et al. | |
| 5,608,039 A | 3/1997 | Pastan et al. | |
| 5,639,641 A | 6/1997 | Pedersen et al. | |
| 5,693,761 A | 12/1997 | Queen et al. | |
| 5,714,352 A | 2/1998 | Jakobovits | |
| 5,821,238 A | 10/1998 | Pastan et al. | |
| 5,854,044 A | 12/1998 | Pastan et al. | |
| 6,265,150 B1 | 7/2001 | Terstappen et al. | |
| 7,396,920 B2 * | 7/2008 | Hemmings ............. | A61P 35/00 536/23.1 |
| 8,871,906 B2 | 10/2014 | Pastan et al. | |
| 8,907,060 B2 | 12/2014 | Pastan et al. | |
| 8,936,792 B2 | 1/2015 | Pastan et al. | |
| 9,206,240 B2 | 12/2015 | Pastan et al. | |
| 9,346,859 B2 | 5/2016 | Pastan et al. | |
| 9,388,222 B2 | 7/2016 | Pastan et al. | |
| 2002/0197266 A1 | 12/2002 | Debinski | |
| 2014/0154248 A1 | 6/2014 | Pastan et al. | |
| 2015/0252118 A1 * | 9/2015 | Ho ..................... | A61K 47/6857 424/156.1 |

FOREIGN PATENT DOCUMENTS

| | | | |
|---|---|---|---|
| EP | 0239400 B1 | 3/1987 | |
| GB | 2188638 A | 10/1987 | |
| WO | WO 2014/052064 A1 | 4/2014 | |

OTHER PUBLICATIONS

Padlan, X-Ray Crystallography of Antibodies, Advances in Protein Chemistry, 1996, 49:57-133.*

(Continued)

*Primary Examiner* — Hong Sang
(74) *Attorney, Agent, or Firm* — Leydig, Voit & Mayer

(57) ABSTRACT

Polypeptides and proteins that specifically bind to and immunologically recognize human mesothelin582-598 (IPNGYLVLDLSMQEALS) (SEQ ID NO: 1) are disclosed. Anti-mesothelin binding moieties, nucleic acids, recombinant expression vectors, host cells, populations of cells, pharmaceutical compositions, and conjugates relating to the polypeptides and proteins are disclosed. Methods of reducing mesothelin shed from cell membranes, methods of reducing the activity of TNFα converting enzyme, methods of detecting the presence of cancer, and methods of treating or preventing cancer are also disclosed.

19 Claims, 9 Drawing Sheets
Specification includes a Sequence Listing.

(56) References Cited

OTHER PUBLICATIONS

Berglund et al., The epitope space of the human proteome, Protein Science, 2008, 17:606-613.*
Goel et al., Plasticity within the Antigen Combining Site May Manifest as Molecular Mimicry in the Humoral Immune Response, The Journal of Immunology, 2004, 173(12):7358-7367.*
Lloyd et al., Modelling the human immune response: performance of a 1011 human antibody repertoire against a broad panel of therapeutically relevant antigens, Protein Engineering, Design & Selection, 2009, 22(3):159-168.*
Edwards et al.,The remarkable flexibility of the human antibody repertoire; isolation of over one thousand different antibodies to a single protein, BlyS. Journal of Molecular Biology, 2003, 334:103-118.*
Paul, Fundamental Immunology, 3rd Edition, 1993, pp. 292-295.*
Rudikoff et al., Proc. Natl. Acad. Sci. USA, 1982, 79(6):1979-1983.*
Colman, Research in Immunology, 1994, 145:33-36.*
Bendig, Methods: A Companion to Methods in Enzymology, 1995; 8:83-93.*
Khantasup et al., Monoclonal Antibodies in Immunodiagnosis and Immunotherapy, 2015, 34(6): 404-417.*
Cancer information from National Institute of Cancer, Apr. 29, 2010, pp. 1-2.*
Vogelstein et al. Nature Medicine, 2004, 10(8): 789-799.*
Asgarov et al., "A new anti-mesothelin antibody targets selectively the membrane-associated form," *MAbs*, 9(3): 567-577 (2017).
Asgarov et al., "Development of more precise and efficient antibodies for cancer targeting: Membrane associated form specific anti-mesothelin antibodies and CAR as an example," *Research Gate*, 216 pgs. (2016).
Awuah et al., "Reduced Shedding of Surface Mesothelin Improves Efficacy of Mesothelin-Targeting Recombinant Immunotoxins," *Mol. Cancer Ther.*, 15(7): 1648-1655 (2016).
Choi et al., "Synthesis and assembly of a cholera toxin B subunit-rotavirus VP7 fusion protein in transgenic potato," *Mol. Biotechnol.*, 31(3): 193-202 (2005).
Clay et al., "Efficient transfer of a tumor antigen-reactive TCR to human peripheral blood lymphocytes confers anti-tumor reactivity," *J. Immunol.*, 163(1): 507-513 (1999).
Hassan et al., "Detection and quantitation of serum mesothelin, a tumor marker for patients with mesothelioma and ovarian cancer," *Clin. Cancer. Res.*, 12(2): 447-453 (2006).
Hassan et al., "Mesothelin Immunotherapy for Cancer: Ready for Prime Time?" *J. Clin. Oncol.*, 34(34): 4171-4179 (2016).
Ho et al., "Mesothelin is shed from tumor cells," *Cancer Epidemiol Biomarkers Prev.*, 15(9): 1751 (2006).
Hudecz, "Synthesis of peptide bioconjugates," *Methods Mol. Biol.*, 298: 209-223 (2005).
Kirin et al., "Amino acid and peptide bioconjugates of copper(II) and zinc(II) complexes with a modified N,N-bis(2-picolyl)amine ligand," *Inorg. Chem.*, 44(15): 5405-5415 (2005).
Pedersen et al., "Comparison of surface accessible residues in human and murine immunoglobulin Fv domains. Implication for humanization of murine antibodies," *J. Mol. Biol.*, 235(3): 959-973 (1994).
Reiter et al., "Engineering interchain disulfide bonds into conserved framework regions of Fv fragments: improved biochemical characteristics of recombinant immunotoxins containing disulfide-stabilized Fv," *Protein Eng.*, 7(5): 697-704 (1994).
Tang et al., "A human single-domain antibody elicits potent anti-tumor activity by targeting an epitope in mesothelin close to the cancer cell surface," *Mol. Cancer Ther.*, 12(4): 416-426 (2013).
Zhang et al., "Cytotoxic activity of immunotoxin SS1P is modulated by TACE-dependent mesothelin shedding," *Cancer Res.*, 71(17): 5915-5922 (2011).
Zhang et al., "New high affinity monoclonal antibodies recognize non-overlapping epitopes on mesothelin for monitoring and treating mesothelioma," *Sci. Rep.*, 5(9928): 1-14 (2015).
Zhao et al., "Primary human lymphocytes transduced with NY-ESO-1 antigen-specific TCR genes recognize and kill diverse human tumor cell lines," *J. Immunol.*, 174(7): 4415-4423 (2005).

* cited by examiner

US 11,390,683 B2

ANTI-MESOTHELIN POLYPEPTIDES AND PROTEINS

CROSS-REFERENCE TO RELATED APPLICATIONS

This patent application is a U.S. National Phase Patent Application of co-pending International Patent Application No. PCT/US2018/033236, filed May 17, 2018, which claims the benefit of U.S. Provisional Patent Application No. 62/508,197 filed May 18, 2017, both of which are hereby incorporated by reference in their entireties.

STATEMENT REGARDING FEDERALLY SPONSORED RESEARCH OR DEVELOPMENT

This invention was made with Government support under project number 1ZIABC008753-35 by the National Institutes of Health, National Cancer Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: one 25,719 Byte ASCII (Text) file named "746717_ST25.txt" dated Nov. 15, 2019.

BACKGROUND OF THE INVENTION

Cancer is a public health concern. Despite advances in treatments such as chemotherapy, the prognosis for many cancers may be poor. Accordingly, there exists an unmet need for additional treatments for cancer.

BRIEF SUMMARY OF THE INVENTION

An embodiment of the invention provides a polypeptide or protein which specifically recognizes and binds to human mesothelin$_{582-598}$(IPNGYLVLDLSMQEALS) (SEQ ID NO: 1).

Another embodiment of the invention provides a polypeptide comprising (i) SEQ ID NOs: 2-7, (ii) SEQ ID NOs: 8-13, or (iii) SEQ ID NOs: 14-19.

Yet another embodiment of the invention provides a protein comprising: (a) a first polypeptide chain comprising SEQ ID NOs: 2-4 and a second polypeptide chain comprising SEQ ID NOs: 5-7; (b) a first polypeptide chain comprising SEQ ID NOs: 8-10 and a second polypeptide chain comprising SEQ ID NOs: 11-13; or (c) a first polypeptide chain comprising SEQ ID NOs: 14-16 and a second polypeptide chain comprising SEQ ID NOs: 17-19.

Further embodiments of the invention provide related anti-mesothelin binding moieties, nucleic acids, recombinant expression vectors, host cells, populations of cells, conjugates, kits, and pharmaceutical compositions relating to the polypeptides and proteins of the embodiments of the invention.

Additional embodiments of the invention provide methods of reducing mesothelin shed from cell membranes, methods of reducing the activity of TNFα converting enzyme, methods of detecting the presence of cancer, and methods of treating or preventing cancer.

BRIEF DESCRIPTION OF THE SEVERAL VIEWS OF THE DRAWINGS

FIG. 2 shows that antibody 15B6 (comprising SEQ ID NOs: 14-19) (squares) bound more strongly to A431/MSLN(M) cells compared to the control antibody MN (diamonds).

FIG. 3 shows that antibody 15B6 (comprising SEQ ID NOs: 14-19) (circles) bound strongly to RH29 cells compared to the control antibody MPC11 (triangles).

FIG. 4 shows that antibody 15B6 (comprising SEQ ID NOs: 14-19) (squares) bound strongly to KLM-1 cells.

DETAILED DESCRIPTION OF THE INVENTION

Figure 1:
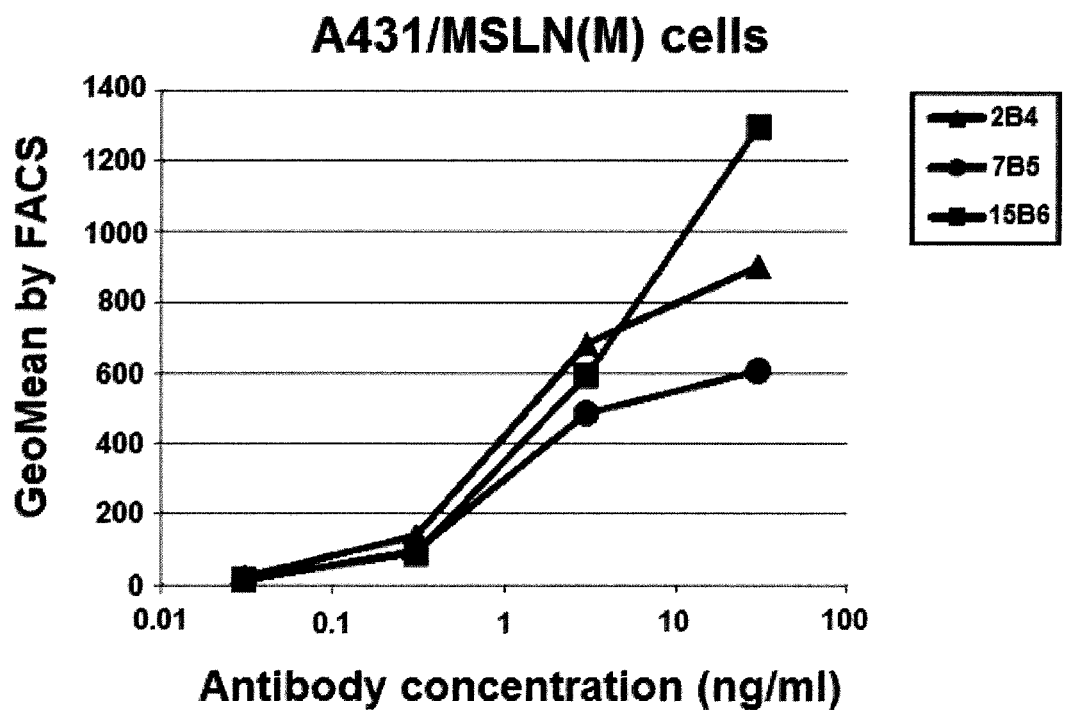
FIG. 1 is a graph showing binding of antibodies to A431/MSLN(M) cells (a cell line transfected with a mesothelin variant with M at position 593) measured (GeoMean) by fluorescence-activated cell sorting ("FACS"). Antibodies 2B4 (comprising SEQ ID NOs: 2-7) (triangles), antibodies 7B5 (comprising SEQ ID NOs: 8-13) (circles), and 15B6 (comprising SEQ ID NOs: 14-19) (squares) are shown for the indicated concentrations.

An embodiment of the invention provides polypeptides and proteins comprising an antigen binding domain of an anti-mesothelin antibody. The polypeptides and proteins advantageously specifically recognize and bind to a specific region of human mesothelin (mesothelin$_{582-598}$ (IPNGYLVLDLSMQEALS) (SEQ ID NO: 1)) or any portion thereof with high affinity, provided that the portion of human mesothelins$_{582}$-598 is at least 5 (e.g., 6, 7, 8, 9, 10, 11, 12, 13, 14, 15, or 16) amino acid residues in length. An embodiment of the invention provides polypeptides and proteins which advantageously specifically recognize and bind to human mesothelin (mesothelin$_{582}$-598(IPNGYLVLDLSMQEALS) (SEQ ID NO: 1)) or any portion thereof with high affinity, provided that the human mesothelin$_{582-598}$ sequence or portion thereof is 5-17, 6-17, 7-17, 8-17, 9-17, 10-17, 11-17, 12-17, 13-17, 14-17, 15-17, 16-17, 5-16, 6-16, 7-16, 8-16, 9-16, 10-16, 11-16, 12-16, 13-16, 14-16, 15-16, 5-15, 6-15, 7-15, 8-15, 9-15, 10-15, 11-15, 12-15, 13-15, 14-15, 5-14, 6-14, 7-14, 8-14, 9-14, 10-14, 11-14, 12-14, 13-14, 5-13, 6-13, 7-13, 8-13, 9-13, 10-13, 11-13, 12-13, 5-12, 6-12, 7-12, 8-12, 9-12, 10-12, 11-12, 5-11, 6-11, 7-11, 8-11, 9-11, 10-11, 5-10, 6-10, 7-10, 8-10, 9-10, 5-9, 6-9, 7-9, 8-9, 5-8, 6-8, 7-8, 5-7, 6-7, or 5-6 amino acids in length. In an embodiment, the portion of human mesothelin$_{582-598}$ comprises LVLDL (SEQ ID NO: 63).

Mesothelin (SEQ ID NO: 56) is expressed by normal, non-tumor, or non-cancerous mesothelial cells lining the pleura, peritoneum, and pericardium and is over-expressed by tumor or cancer cells from a variety of different cancers such as, e.g., ovarian cancer, pancreatic cancer, lung cancer (e.g., lung adenocarcinoma), esophageal cancer, gastric cancer, synovial sarcoma, and mesothelioma. The expression of mesothelin by normal, non-tumor, or non-cancerous cells is not as robust as the expression by tumor or cancer cells. In this regard, the tumor or cancer cells can over-express mesothelin or express mesothelin at a significantly higher level, as compared to the expression of mesothelin by normal, non-tumor, or non-cancerous cells.

Mesothelin is constantly shed from cells by TNFα converting enzyme (TACE; also referred to as "ADAM17") leaving behind only a short protein fragment on the cell surface. There are two TACE cleavage sites in mesothelin which are five amino acid residues apart. TACE may cleave mesothelin at either of the two cleavage sites. The first TACE cleavage site is positioned between amino acid residues 586 and 587. Cleavage at the first TACE cleavage site yields a portion of mesothelin having the terminal sequence of 566-QRQDDLDTLGLGLQGGIPNGY-586 (SEQ ID NO: 57) that is released from the cell and a portion of mesothelin left associated with the cell surface which has the terminal sequence of 587-LVLDLSMQEALS-598 (SEQ ID NO: 58). The second TACE cleavage site is positioned between amino acid residues 591 and 592. Cleavage at the second TACE cleavage site yields a portion of mesothelin having the terminal sequence of 566-QRQDDLDTLGLGLQGGIPNGYLVLDL-591 (SEQ ID NO: 59) that is released from the cell and a portion of mesothelin left associated with the cell surface which has the terminal sequence of 592-SMQEALS-598 (SEQ ID NO: 60). Antibodies that bind to the shed portions of mesothelin may be rapidly released from the cell and may lose their effector function.

In an embodiment of the invention, the inventive polypeptides and proteins may elicit an antigen-specific response against mesothelin$_{582-598}$ (IPNGYLVLDLSMQEALS) (SEQ ID NO: 1). Accordingly, without being bound to a particular theory or mechanism, it is believed that by specifically recognizing and binding mesothelin$_{582-598}$ (IPNGYLVLDLSMQEALS) (SEQ ID NO: 1), the inventive proteins and polypeptides may provide for one or more of the following: detecting mesothelin-expressing cancer cells, targeting and destroying mesothelin-expressing cancer cells, reducing or eliminating cancer cells, facilitating infiltration of immune cells and/or effector molecules to tumor site(s), enhancing/extending anti-cancer responses, reducing or preventing the shedding of mesothelin from cells, and reducing or preventing the activity of TACE. By recognizing and binding to mesothelin$_{582-598}$ (IPNGYLVLDLSMQEALS) (SEQ ID NO: 1), the inventive polypeptides and proteins may remain associated with the cancer cell for longer periods of time and may be more effective in killing cancer cells as compared to, for example, those antibodies which bind to the portion of mesothelin which is shed from the cell and which bind at a position that is more distal from the TACE cleavage sites than mesothelin$_{582-598}$ (IPNGYLVLDLSMQEALS) (SEQ ID NO: 1).

An embodiment of the invention provides a polypeptide which specifically recognizes and binds to human mesothelin$_{582-598}$ (IPNGYLVLDLSMQEALS) (SEQ ID NO: 1). The term "polypeptide" as used herein includes oligopeptides and refers to a single chain of amino acids connected by one or more peptide bonds. The polypeptide may comprise one or more variable regions (e.g., two variable regions) of an antigen binding domain of an anti-mesothelin antibody, each variable region comprising a complementarity determining region (CDR) 1, a CDR2, and a CDR3. The polypeptide can comprise the CDRs (i) SEQ ID NOs: 2-7, (ii) SEQ ID NOs: 8-13, or (iii) SEQ ID NOs: 14-19.

An embodiment of the invention provides a polypeptide comprising the CDR regions of the 2B4 anti-mesothelin antibody. In this regard, the polypeptide may comprise a first variable region comprising a CDR1 comprising the amino acid sequence of SEQ ID NO: 2 (CDR1 of first variable region), a CDR2 comprising the amino acid sequence of SEQ ID NO: 3 (CDR2 of first variable region), and a CDR3 comprising the amino acid sequence of SEQ ID NO: 4 (CDR3 of first variable region), and a second variable region comprising a CDR1 comprising the amino acid sequence of SEQ ID NO: 5 (CDR1 of second variable region), a CDR2 comprising the amino acid sequence of SEQ ID NO: 6 (CDR2 of second variable region), and a CDR3 comprising the amino acid sequence of SEQ ID NO: 7 (CDR3 of second variable region). In this regard, the inventive polypeptide can comprise (i) all of SEQ ID NOs: 2-4, (ii) all of SEQ ID NOs: 5-7, or (iii) all of SEQ ID NOs: 2-7. Preferably, the polypeptide comprises all of SEQ ID NOs: 2-7.

In an embodiment of the invention, the polypeptide comprising the CDR regions of the 2B4 anti-mesothelin antibody further comprises the framework regions of the 2B4 anti-mesothelin antibody. In this regard, the polypeptide comprising the CDR regions of the 2B4 anti-mesothelin antibody further comprises the amino acid sequence of SEQ ID NO: 32 (framework region ("FR") 1 of first variable region), the amino acid sequence of SEQ ID NO: 33 (FR2 of first variable region), the amino acid sequence of SEQ ID NO: 34 (FR3 of first variable region), the amino acid sequence of SEQ ID NO: 35 (FR4 of first variable region), the amino acid sequence of SEQ ID NO: 36 (FR1 of second variable region), the amino acid sequence of SEQ ID NO: 37 (FR2 of second variable region), the amino acid sequence of SEQ ID NO: 38 (FR3 of second variable region), and the amino acid sequence of SEQ ID NO: 39 (FR4 of second variable region). In this regard, the inventive polypeptide can comprise (i) all of SEQ ID NOs: 2-4 and 32-35, (ii) all of SEQ ID NOs: 5-7 and 36-39; or (iii) all of SEQ ID NOs: 2-7 and 32-39.

An embodiment of the invention provides a polypeptide comprising the CDR regions of the 7B5 anti-mesothelin antibody. In this regard, the polypeptide may comprise a first variable region comprising a CDR1 comprising the amino acid sequence of SEQ ID NO: 8 (CDR1 of first variable region), a CDR2 comprising the amino acid sequence of SEQ ID NO: 9 (CDR2 of first variable region), and a CDR3 comprising the amino acid sequence of SEQ ID NO: 10 (CDR3 of first variable region), and a second variable region comprising a CDR1 comprising the amino acid sequence of SEQ ID NO: 11 (CDR1 of second variable region), a CDR2 comprising the amino acid sequence of SEQ ID NO: 12 (CDR2 of second variable region), and a CDR3 comprising the amino acid sequence of SEQ ID NO: 13 (CDR3 of second variable region). In this regard, the inventive polypeptide can comprise (i) all of SEQ ID NOs: 8-10, (ii) all of SEQ ID NOs: 11-13, or (iii) all of SEQ ID NOs: 8-13. Preferably, the polypeptide comprises all of SEQ ID NOs: 8-13.

In an embodiment of the invention, the polypeptide comprising the CDR regions of the 7B5 anti-mesothelin antibody further comprises the framework regions of the 7B5 anti-mesothelin antibody. In this regard, the polypeptide comprising the CDR regions of the 7B5 anti-mesothelin antibody further comprises the amino acid sequence of SEQ ID NO: 40 (FR1 of first variable region), the amino acid sequence of SEQ ID NO: 41 (FR2 of first variable region), the amino acid sequence of SEQ ID NO: 42 (FR3 of first variable region), the amino acid sequence of SEQ ID NO: 43 (FR4 of first variable region), the amino acid sequence of SEQ ID NO: 44 (FR1 of second variable region), the amino acid sequence of SEQ ID NO: 45 (FR2 of second variable region), the amino acid sequence of SEQ ID NO: 46 (FR3 of second variable region), and the amino acid sequence of SEQ ID NO: 47 (FR4 of second variable region). In this regard, the inventive polypeptide can comprise (i) all of SEQ ID NOs: 8-10 and 40-43, (ii) all of SEQ ID NOs: 11-13 and 44-47; or (iii) all of SEQ ID NOs: 8-13 and 40-47.

An embodiment of the invention provides a polypeptide comprising the CDR regions of the 15B6 anti-mesothelin antibody. In this regard, the polypeptide may comprise a first variable region comprising a CDR1 comprising the amino acid sequence of SEQ ID NO: 14 (CDR1 of first variable region), a CDR2 comprising the amino acid sequence of SEQ ID NO: 15 (CDR2 of first variable region), and a CDR3 comprising the amino acid sequence of SEQ ID NO: 16 (CDR3 of first variable region), and a second variable region comprising a CDR1 comprising the amino acid sequence of SEQ ID NO: 17 (CDR1 of second variable region), a CDR2 comprising the amino acid sequence of SEQ ID NO: 18 (CDR2 of second variable region), and a CDR3 comprising the amino acid sequence of SEQ ID NO: 19 (CDR3 of second variable region). In this regard, the inventive polypeptide can comprise (i) all of SEQ ID NOs: 14-16, (ii) all of SEQ ID NOs: 17-19, or (iii) all of SEQ ID NOs: 14-19. Preferably, the polypeptide comprises all of SEQ ID NOs: 14-19.

In an embodiment of the invention, the polypeptide comprising the CDR regions of the 15B6 anti-mesothelin antibody further comprises the framework regions of the 15B6 anti-mesothelin antibody. In this regard, the polypeptide comprising the CDR regions of the 15B6 anti-mesothelin antibody further comprises the amino acid sequence of SEQ ID NO: 48 (FR1 of first variable region), the amino acid sequence of SEQ ID NO: 49 (FR2 of first variable region), the amino acid sequence of SEQ ID NO: 50 (FR3 of first variable region), the amino acid sequence of SEQ ID NO: 51 (FR4 of first variable region), the amino acid sequence of SEQ ID NO: 52 (FR1 of second variable region), the amino acid sequence of SEQ ID NO: 53 (FR2 of second variable region), the amino acid sequence of SEQ ID NO: 54 (FR3 of second variable region), and the amino acid sequence of SEQ ID NO: 55 (FR4 of second variable region). In this regard, the inventive polypeptide can comprise (i) all of SEQ ID NOs: 14-16 and 48-51, (ii) all of SEQ ID NOs: 17-19 and 52-55; or (iii) all of SEQ ID NOs: 14-19 and 48-55.

In an embodiment, each respective polypeptide comprises one or more variable regions (e.g., first and second variable regions) of an antigen binding domain of an anti-mesothelin antibody, each variable region comprising the respective CDRs as described above. In an embodiment of the invention, the first variable region is the heavy chain of an anti-mesothelin antibody and the second variable region is the light chain of an anti-mesothelin antibody.

An embodiment of the invention provides a polypeptide comprising one or both variable regions of the 2B4 anti-mesothelin antibody. In this regard, the first variable region may comprise SEQ ID NO: 20. The second variable region may comprise SEQ ID NO: 21. Accordingly, in an embodiment of the invention, the polypeptide comprises SEQ ID NO: 20, SEQ ID NO: 21, or both SEQ ID NOs: 20 and 21. Preferably, the polypeptide comprises both of SEQ ID NOs: 20-21.

An embodiment of the invention provides a polypeptide comprising one or both variable regions of the 7B5 anti-mesothelin antibody. In this regard, the first variable region may comprise SEQ ID NO: 22. The second variable region may comprise SEQ ID NO: 23. Accordingly, in an embodiment of the invention, the polypeptide comprises SEQ ID NO: 22, SEQ ID NO: 23, or both SEQ ID NOs: 22 and 23. Preferably, the polypeptide comprises both of SEQ ID NOs: 22-23.

An embodiment of the invention provides a polypeptide comprising one or both variable regions of the 15B6 anti-mesothelin antibody. In this regard, the first variable region may comprise SEQ ID NO: 24. The second variable region may comprise SEQ ID NO: 25. Accordingly, in an embodiment of the invention, the polypeptide comprises SEQ ID NO: 24, SEQ ID NO: 25, or both SEQ ID NOs: 24 and 25. Preferably, the polypeptide comprises both of SEQ ID NOs: 24-25.

An embodiment of the invention provides a protein which specifically recognizes and binds to human mesothelin$_{582-598}$(IPNGYLVLDLSMQEALS) (SEQ ID NO: 1). The protein may comprise at least one of the polypeptides described herein. By "protein" it is meant a molecule comprising one or more polypeptide chains.

In an embodiment, the protein can comprise (a) a first polypeptide chain comprising SEQ ID NOs: 2-4 and a second polypeptide chain comprising SEQ ID NOs: 5-7; (b) a first polypeptide chain comprising SEQ ID NOs: 8-10 and a second polypeptide chain comprising SEQ ID NOs: 11-13; or (c) a first polypeptide chain comprising SEQ ID NOs: 14-16 and a second polypeptide chain comprising SEQ ID NOs: 17-19. In an embodiment of the invention, the protein may comprise (a) a first polypeptide chain comprising SEQ ID NO: 20 and a second polypeptide chain comprising SEQ ID NO: 21; (b) a first polypeptide chain comprising SEQ ID NO: 22 and a second polypeptide chain comprising SEQ ID NO: 23; or (c) a first polypeptide chain comprising SEQ ID NO: 24 and a second polypeptide chain comprising SEQ ID NO: 25.

In an embodiment, the protein can comprise (a) a first polypeptide chain comprising SEQ ID NOs: 2-4 and SEQ ID NOs: 32-35 and a second polypeptide chain comprising SEQ ID NOs: 5-7 and SEQ ID NOs: 36-39; (b) a first polypeptide chain comprising SEQ ID NOs: 8-10 and SEQ ID NOs: 40-43 and a second polypeptide chain comprising SEQ ID NOs: 11-13 and SEQ ID NOs: 44-47; or (c) a first polypeptide chain comprising SEQ ID NOs: 14-16 and SEQ ID NOs: 48-51 and a second polypeptide chain comprising SEQ ID NOs: 17-19 and SEQ ID NOs: 52-55.

In an embodiment, the protein can be, for example, a fusion protein. If, for example, the protein comprises a single polypeptide chain comprising (a) a first polypeptide chain comprising SEQ ID NOs: 2-4 and a second polypeptide chain comprising SEQ ID NOs: 5-7; (b) a first polypeptide chain comprising SEQ ID NOs: 8-10 and a second polypeptide chain comprising SEQ ID NOs: 11-13; or (c) a first polypeptide chain comprising SEQ ID NOs: 14-16 and a second polypeptide chain comprising SEQ ID NOs: 17-19, or if the first and/or second polypeptide chain(s) of the protein further comprise(s) other amino acid sequences, e.g., an amino acid sequence encoding an immunoglobulin or a portion thereof, then the inventive protein can be a fusion protein. In this regard, an embodiment of the invention also provides a fusion protein comprising at least one of the inventive polypeptides described herein along with at least one other polypeptide. The other polypeptide can exist as a separate polypeptide of the fusion protein, or can exist as a polypeptide, which is expressed in frame (in tandem) with one of the inventive polypeptides described herein. The other polypeptide can encode any peptidic or proteinaceous molecule, or a portion thereof, including, but not limited to an immunoglobulin, CD3, CD4, CD8, an MHC molecule, a CD1 molecule, e.g., CD1a, CD1b, CD1c, CD1d, etc.

The fusion protein can comprise one or more copies of the inventive polypeptide and/or one or more copies of the other polypeptide. For instance, the fusion protein can comprise 1, 2, 3, 4, 5, or more, copies of the inventive polypeptide and/or of the other polypeptide. Suitable methods of making fusion proteins are known in the art, and include, for example, recombinant methods. See, for instance, Choi et al., *Mol. Biotechnol.* 31: 193-202 (2005).

It is contemplated that the polypeptides and proteins may be useful as anti-mesothelin binding moieties. In this regard, an embodiment of the invention provides an anti-mesothelin binding moiety comprising any of the polypeptides or proteins described herein. In an embodiment of the invention, the anti-mesothelin binding moiety comprises an antigen binding portion of any of the polypeptides or proteins described herein. The antigen binding portion can be any portion that has at least one antigen binding site. In an embodiment, the anti-mesothelin binding moiety is an antibody, a Fab fragment (Fab), F(ab')$_2$ fragment, diabody, triabody, tetrabody, bispecific antibody, single-chain variable region fragment (scFv), or disulfide-stabilized variable region fragment (dsFv).

In an embodiment, the anti-mesothelin binding moiety is an antibody. The antibody may be, for example, a recombinant antibody comprising at least one of the inventive polypeptides or proteins described herein. As used herein, "recombinant antibody" refers to a recombinant (e.g., genetically engineered) protein comprising at least one of the inventive polypeptides or proteins and one or more polypeptide chains of an antibody, or a portion thereof. The polypeptide of an antibody, or portion thereof, can be, for example, a constant region of a heavy or light chain, or an Fc fragment of an antibody, etc. The polypeptide chain of an antibody, or portion thereof, can exist as a separate polypeptide of the recombinant antibody. Alternatively, the polypeptide chain of an antibody, or portion thereof, can exist as a polypeptide, which is expressed in frame (in tandem) with the polypeptide or protein. The polypeptide of an antibody, or portion thereof, can be a polypeptide of any antibody or any antibody fragment.

The antibody of an embodiment of the invention can be any type of immunoglobulin that is known in the art. For instance, the anti-mesothelin binding moiety can be an antibody of any isotype, e.g., IgA, IgD, IgE, IgG (e.g., IgG1, IgG2, IgG3, or IgG4), IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. Also, the antibody can have any level of affinity or avidity for mesothelin.

Methods of testing antibodies for the ability to bind to mesothelin are known in the art and include any antibody-antigen binding assay, such as, for example, radioimmunoassay ("RIA"), enzyme-linked immunosorbent assay ("ELISA"), Western blot, immunoprecipitation, and competitive inhibition assays (see, e.g., Murphy et al., infra, and U.S. Patent Application Publication No. 2002/0197266 A1).

Suitable methods of making antibodies are known in the art. For instance, standard hybridoma methods are described in, e.g., *Antibodies: A Laboratory Manual*, 2$^{nd}$ Ed., CSH Press (2013), and Murphy et al. (eds.), *Janeway's Immunobiology*, 9$^{th}$ Ed., Taylor & Francis, Inc., New York, N.Y. (2016). Alternatively, other methods, such as Epstein-Barr virus (EBV)-hybridoma methods and bacteriophage vector expression systems are known in the art. Further, methods of producing antibodies in non-human animals are described in, e.g., U.S. Pat. Nos. 5,545,806, 5,569,825, and 5,714,352, and U.S. Patent Application Publication No. 2002/0197266 A1.

Phage display furthermore can be used to generate an antibody. In this regard, phage libraries encoding antigen-binding variable (V) domains of antibodies can be generated using standard molecular biology and recombinant DNA techniques. See, for instance, Green et al. (eds.), *Molecular Cloning, A Laboratory Manual*, 4$^{th}$ Edition, Cold Spring Harbor Laboratory Press, New York (2012) and Ausubel et al., *Current Protocols in Molecular Biology*, Greene Publishing Associates and John Wiley & Sons, NY (2007). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Murphy et al., supra, Huse et al., supra, and U.S. Pat. No. 6,265,150).

Antibodies can be produced by transgenic mice that are transgenic for specific heavy and light chain immunoglobulin genes. Such methods are known in the art and described in, for example U.S. Pat. Nos. 5,545,806 and 5,569,825, and Murphy et al., supra.

Methods for generating humanized antibodies are well known in the art and are described in detail in, for example, Murphy et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in U.S. Pat. No. 5,639,641 and Pedersen et al., *J. Mol. Biol.*, 235, 959-973 (1994).

In a preferred embodiment, the anti-mesothelin binding moiety is a single-chain variable region fragment (scFv). A single-chain variable region fragment (scFv), which is a truncated Fab fragment including the variable (V) domain of an antibody heavy chain linked to a V domain of a light antibody chain via a synthetic peptide, can be generated using routine recombinant DNA technology techniques (see, e.g., Murphy et al., supra). Similarly, disulfide-stabilized variable region fragments (dsFv) can be prepared by recombinant DNA technology (see, e.g., Reiter et al., *Protein Engineering*, 7: 697-704 (1994)). The anti-mesothelin binding moieties of embodiments of the invention, however, are not limited to these exemplary types of antibody fragments.

Also, the anti-mesothelin binding moiety can be modified to comprise a detectable label, such as, for instance, a radioisotope, a fluorophore (e.g., fluorescein isothiocyanate (FITC), phycoerythrin, an enzyme (e.g., alkaline phosphatase, horseradish peroxidase), and element particles (e.g., gold particles).

Included in the scope of the embodiments of the invention are functional portions of the inventive polypeptides and proteins described herein. The term "functional portion" when used in reference to a polypeptide or protein refers to any part or fragment of the polypeptide or protein of the embodiments of the invention, which part or fragment retains the biological activity of the polypeptide or protein of which it is a part (the parent polypeptide or protein). Functional portions encompass, for example, those parts of a polypeptide or protein that retain the ability to recognize target cells, or detect, treat, or prevent cancer, to a similar extent, the same extent, or to a higher extent, as the parent polypeptide or protein. In reference to the parent polypeptide or protein, the functional portion can comprise, for instance, about 10%, 25%, 30%, 50%, 68%, 80%, 90%, 95%, or more, of the parent polypeptide or protein.

The functional portion can comprise additional amino acids at the amino or carboxy terminus of the portion, or at both termini, which additional amino acids are not found in the amino acid sequence of the parent polypeptide or protein. Desirably, the additional amino acids do not interfere with the biological function of the functional portion, e.g., to recognize target cells, reduce mesothelin shed from cells, reduce TACE activity in mammals, detect cancer, treat or prevent cancer, etc. More desirably, the additional amino acids enhance the biological activity, as compared to the biological activity of the parent polypeptide or protein.

Included in the scope of the embodiments of the invention are functional variants of the inventive polypeptides or proteins described herein. The term "functional variant" as used herein refers to a polypeptide or protein having substantial or significant sequence identity or similarity to a parent polypeptide or protein, which functional variant retains the biological activity of the polypeptide or protein of which it is a variant. Functional variants encompass, for example, those variants of the polypeptide or protein described herein (the parent polypeptide or protein) that retain the ability to recognize target cells to a similar extent, the same extent, or to a higher extent, as the parent polypeptide or protein. In reference to the parent polypeptide or protein, the functional variant can, for instance, be at least about 30%, about 50%, about 75%, about 80%, about 85%, about 90%, about 91%, about 92%, about 93%, about 94%, about 95%, about 96%, about 97%, about 98%, about 99% or more identical in amino acid sequence to the parent polypeptide or protein.

A functional variant can, for example, comprise the amino acid sequence of the parent polypeptide or protein with at least one conservative amino acid substitution. Alternatively or additionally, the functional variants can comprise the amino acid sequence of the parent polypeptide or protein with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent polypeptide or protein.

Amino acid substitutions of the inventive polypeptides or proteins are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gln, Ser, Thr, Tyr, etc.), an amino acid with a beta-branched side-chain substituted for another amino acid with a beta-branched side-chain (e.g., Ile, Thr, and Val), an amino acid with an aromatic side-chain substituted for another amino acid with an aromatic side chain (e.g., His, Phe, Trp, and Tyr), etc.

The polypeptide or protein can consist essentially of the specified amino acid sequence or sequences described herein, such that other components, e.g., other amino acids, do not materially change the biological activity of the polypeptide, protein, functional portion, or functional variant.

The polypeptides or proteins of embodiments of the invention (including functional portions and functional variants) can be of any length, i.e., can comprise any number of amino acids, provided that the polypeptides or proteins (or functional portions or functional variants thereof) retain their biological activity, e.g., the ability to specifically bind to antigen, detect cancer cells in a mammal, or treat or prevent cancer in a mammal, etc. For example, the polypeptide or protein can be about 50 to about 5,000 amino acids long, such as 50, 70, 75, 100, 125, 150, 175, 200, 300, 400, 500, 600, 700, 800, 900, 1,000, or more amino acids in length.

The polypeptides or proteins of embodiments of the invention (including functional portions and functional variants of the invention) can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3-and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The polypeptides or proteins of embodiments of the invention (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized.

The polypeptides or proteins of embodiments of the invention (including functional portions and functional variants thereof) can be obtained by methods known in the art. The polypeptides or proteins may be made by any suitable method of making polypeptides or proteins. Suitable methods of de novo synthesizing polypeptides and proteins are described in references, such as Chan et al., *Fmoc Solid Phase Peptide Synthesis*, Oxford University Press, Oxford, United Kingdom, 2000; *Peptide and Protein Drug Analysis*, ed. Reid, R., Marcel Dekker, Inc., 2000; *Epitope Mapping*, ed. Westwood et al., Oxford University Press, Oxford, United Kingdom, 2001; and U.S. Pat. No. 5,449,752. Also, polypeptides and proteins can be recombinantly produced using the nucleic acids described herein using standard recombinant methods. See, e.g., Green et al., supra, and Ausubel et al., supra. Further, some of the polypeptides or proteins of the embodiments of the invention (including functional portions and functional variants thereof) can be isolated and/or purified from a source, such as a plant, a bacterium, an insect, a mammal, e.g., a rat, a human, etc. Methods of isolation and purification are well-known in the art. Alternatively, the polypeptides or proteins described herein (including functional portions and functional variants thereof) can be commercially synthesized by companies, such as Synpep (Dublin, Calif.), Peptide Technologies Corp. (Gaithersburg, Md.), and Multiple Peptide Systems (San Diego, Calif.). In this respect, the inventive polypeptides or proteins can be synthetic, recombinant, isolated, and/or purified.

Included in the scope of the embodiments of the invention are conjugates, e.g., bioconjugates, comprising any of the inventive polypeptides, proteins, anti-mesothelin binding moieties, functional portions, or functional variants thereof. Conjugates, as well as methods of synthesizing conjugates in general, are known in the art (See, for instance, Hudecz, F., *Methods Mol. Biol.* 298: 209-223 (2005) and Kirin et al., *Inorg Chem.* 44(15): 5405-5415 (2005)). In this regard, an embodiment of the invention provides a conjugate comprising (a) any of the polypeptides, proteins, or anti-mesothelin binding moieties described herein conjugated or fused to (b) an effector molecule. The effector molecule may be any therapeutic molecule or a molecule that facilitates the detection of the conjugate such as a drug, toxin, label (e.g., any of the detectable labels described herein), small molecule, or another antibody. For example, the toxin may be Pseudomonas exotoxin A ("PE") or variants thereof such as, e.g., any of PE24, PE4E, PE40, PE38, PE25, PE38QQR, PE38KDEL, PE-LR, and PE35, as described in, e.g., U.S. Pat. Nos. 4,892,827; 5,512,658; 5,602,095; 5,608,039; 5,821,238; 5,854,044; and 8,871,906, each of which is incorporated herein by reference. PE variants include PE which has been modified to remove B cell and/or T-cell epitopes to reduce the immunogenicity of the PE as described in, for example, any of U.S. Pat. Nos. 9,206,240; 9,346,859; 9,388,222; 8,907,060; 8,871,906; 8,936,792; and U.S. Patent Publication No. 2014/154248, each of which is incorporated herein by reference. PE is a bacterial toxin with cytotoxic activity that may be effective for destroying or inhibiting the growth of undesireable cells, e.g., cancer cells. Accordingly, PE may be useful for treating or preventing diseases such as cancer.

Examples of drugs that may be suitable in the inventive conjugates include, but are not limited to, pyrrolobenzodiazepine (PBD) dimer, tubulin-binders such as, for example, dolastatin 10, monomethyl dolastatin 10, auristain E, monomethyl auristain E (MMAE), auristatin F, monomethyl auristatin F, HTI-286, tubulysin M, maytansinoid AP-3, cryptophycin, Boc-Val-Dil-Dap-OH, tubulysin IM-1, Boc-Val-Dil-Dap-Phe-OMe, tubulysin IM-2, Boc-Nme-Val-Val-Dil-Dap-OH, tubulysin IM-3, and colchicine DA; DNA-alkylators(duocarmycin analogs) such as, for example, duocarmycin SA, duocarmycin CN, duocarmycin DMG, duocarmycin DMA, duocarmycin MA, duocarmycin TM, duocarmycin MB, duocarmycin GA; tomaymycin DM; SJG-136; illudin S; irofulven; apaziquone; triptolide; staurosporine; camptothecin; methotrexate; and other anti-cancer drugs such as, for example, kinase inhibitors, histone deacetylase (HDAC) inhibitors, proteasome inhibitors, and matrix metalloproteinase (MMP) inhibitors. In an embodiment, the drug is MMAE or PBD dimer.

The polypeptides, proteins, or anti-mesothelin binding moieties described herein may be conjugated or fused to (b) an effector molecule (such as a drug, toxin, label, small molecule, or an antibody) directly or indirectly, e.g., via a linking moiety. The linking moiety may be any suitable linking moiety known in the art. In an embodiment, the linking moiety is a cleavable linker that may be cleaved upon administration of the conjugate to a mammal.

Further provided by an embodiment of the invention is a nucleic acid comprising a nucleotide sequence encoding any of the polypeptides, proteins, anti-mesothelin binding moieties, conjugates, or functional portions or functional variants thereof.

An embodiment of the invention provides a nucleic acid comprising a nucleotide sequence encoding any of the polypeptides, proteins, or anti-mesothelin binding moieties described herein. In this regard, the nucleic acid comprises a nucleotide sequence encoding first and second variable regions (i) SEQ ID NOs: 26 and 27 (2B4 antibody), (ii) SEQ ID NOs: 28 and 29 (7B5 antibody), or (iii) SEQ ID NOs: 30 and 31 (15B6 antibody), respectively.

"Nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable in some instances, as discussed herein, for the nucleic acid to comprise one or more insertions, deletions, inversions, and/or substitutions. In some embodiments, the nucleic acid may encode additional amino acid sequences that do not affect the function of the polypeptide or protein and which may or may not be translated upon expression of the nucleic acid by a host cell. In an embodiment of the invention, the nucleic acid is complementary DNA (cDNA). In an embodiment of the invention, the nucleic acid comprises a codon-optimized nucleotide sequence.

The nucleic acids of an embodiment of the invention may be recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can consist essentially of the specified nucleotide sequence or sequences described herein, such that other components, e.g., other nucleotides, do not materially change the biological activity of the encoded polypeptide, protein, anti mesothelin-binding moieties, functional portion, or functional variant.

A recombinant nucleic acid may be one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques, such as those described in Green et al., supra. The nucleic acids can be constructed based on chemical synthesis and/or enzymatic ligation reactions using procedures known in the art. See, for example, Green et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the embodiments of the invention can be purchased from companies, such as Macromolecular Resources (Fort Collins, Colo.) and Synthegen (Houston, Tex.).

The nucleic acid can comprise any isolated or purified nucleotide sequence which encodes any of the polypeptides, proteins, anti-mesothelin binding moieties, conjugates, or functional portions or functional variants thereof. Alternatively, the nucleotide sequence can comprise a nucleotide sequence which is degenerate to any of the sequences or a combination of degenerate sequences.

An embodiment of the invention also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions may hybridize under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive polypeptides, proteins, anti-mesothelin binding moieties, conjugates, or functional portions or functional variants thereof. It is generally appreciated that conditions can be rendered more stringent by the addition of increasing amounts of formamide.

The embodiments of the invention also provide a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein.

In an embodiment, the nucleic acids of the embodiments of the invention can be incorporated into a recombinant expression vector. In this regard, an embodiment of the invention provides recombinant expression vectors comprising any of the nucleic acids of the invention. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the embodiments of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. Preferably, the non-naturally occurring or altered nucleotides or internucleotide linkages do not hinder the transcription or replication of the vector.

In an embodiment, the recombinant expression vector can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences, Glen Burnie, Md.), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM, and pMAMneo (Clontech). The recombinant expression vector may be a viral vector, e.g., a retroviral vector.

A number of transfection techniques are generally known in the art. Transfection methods include calcium phosphate co-precipitation, direct micro injection into cultured cells, electroporation, liposome mediated gene transfer, lipid mediated transduction, and nucleic acid delivery using high velocity microprojectiles.

In an embodiment, the recombinant expression vectors can be prepared using standard recombinant DNA techniques described in, for example, Green et al., supra, and Ausubel et al., supra. Constructs of expression vectors, which are circular or linear, can be prepared to contain a replication system functional in a prokaryotic or eukaryotic host cell. Replication systems can be derived, e.g., from ColE1, 2 μ plasmid, λ, SV40, bovine papilloma virus, and the like.

The recombinant expression vector may comprise regulatory sequences, such as transcription and translation initiation and termination codons, which are specific to the type of host cell (e.g., bacterium, fungus, plant, or animal) into which the vector is to be introduced, as appropriate, and taking into consideration whether the vector is DNA- or RNA-based. The recombinant expression vector may comprise restriction sites to facilitate cloning.

The recombinant expression vector can include one or more marker genes, which allow for selection of transformed or transfected host cells. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the polypeptides, proteins, anti-mesothelin binding moieties, conjugates, or functional portions or functional variants thereof, or to the nucleotide sequence which is complementary to or which hybridizes to the nucleotide sequence encoding the inventive polypeptides, proteins, anti-mesothelin binding moieties, conjugates, or functional portions or functional variants thereof. The selection of promoters, e.g., strong, weak, inducible, tissue-specific and developmental-specific, is within the ordinary skill of the artisan. Similarly, the combining of a nucleotide sequence with a promoter is also within the ordinary skill of the artisan. The promoter can be a non-viral promoter or a viral promoter, e.g., a cytomegalovirus (CMV) promoter, an SV40 promoter, an RSV promoter, or a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, *Suicide Gene Therapy: Methods and Reviews*, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

An embodiment of the invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α E. coli cells, Chinese hamster ovarian cells, monkey VERO cells, COS cells, HEK293 cells, and the like. For purposes of amplifying or replicating the recombinant expression vector, the host cell may be a prokaryotic cell, e.g., a DH5α cell. For purposes of producing a recombinant polypeptide, protein, anti-mesothelin binding moiety, conjugate, or functional portion or functional variant thereof, the host cell may be a mammalian cell. The host cell may be a human cell. While the host cell can be of any cell type, can originate from any type of tissue, and can be of any developmental stage, the host cell may be a peripheral blood lymphocyte (PBL) or a peripheral blood mononuclear cell (PBMC). The host cell may be a B cell or a T cell.

Also provided by an embodiment of the invention is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

The polypeptides and proteins (including functional portions and variants thereof), nucleic acids, recombinant expression vectors, host cells (including populations thereof), anti-mesothelin binding moieties, and conjugates, all of which are collectively referred to as "inventive anti-mesothelin materials" hereinafter, can be isolated and/or purified. The term "isolated" as used herein means having been removed from its natural environment. The term "purified" or "isolated" does not require absolute purity or isolation; rather, it is intended as a relative term. Thus, for example, a purified (or isolated) host cell preparation is one in which the host cell is more pure than cells in their natural environment within the body. Such host cells may be produced, for example, by standard purification techniques. In some embodiments, a preparation of a host cell is purified such that the host cell represents at least about 50%, for example, at least about 70%, of the total cell content of the preparation. For example, the purity can be at least about 50%, can be greater than about 60%, about 70% or about 80%, or can be about 100%.

The inventive anti-mesothelin materials can be formulated into a composition, such as a pharmaceutical composition. In this regard, an embodiment of the invention provides a pharmaceutical composition comprising any of the inventive anti-mesothelin materials described herein and a pharmaceutically acceptable carrier. The inventive pharmaceutical compositions containing any of the inventive anti-mesothelin materials can comprise more than one inventive anti-mesothelin material, e.g., a conjugate and a nucleic acid, or two or more different conjugates. Alternatively, the pharmaceutical composition can comprise an inventive anti-mesothelin material in combination with other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

With respect to pharmaceutical compositions, the pharmaceutically acceptable carrier can be any of those conventionally used and is limited only by chemico-physical considerations, such as solubility and lack of reactivity with the active agent(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular inventive anti-mesothelin material, as well as by the particular method used to administer the inventive anti-mesothelin material. Accordingly, there are a variety of suitable formulations of the pharmaceutical composition of the embodiments of the invention. Preservatives may be used. Suitable preservatives may include, for example, methylparaben, propylparaben, sodium benzoate, and benzalkonium chloride. A mixture of two or more preservatives optionally may be used. The preservative or mixtures thereof are typically present in an amount of about 0.0001% to about 2% by weight of the total composition.

Suitable buffering agents may include, for example, histidine or citrate-based buffers. Suitable buffering agents may include, for example, citric acid, sodium citrate, phosphoric acid, potassium phosphate, and various other acids and salts. A mixture of two or more buffering agents optionally may be used. The buffering agent or mixtures thereof are typically present in an amount of about 0.001% to about 4% by weight of the total composition.

The concentration of inventive anti-mesothelin material in the pharmaceutical formulations can vary, e.g., from less than about 1%, (e.g., at or at least about 4%) to as much as, for example, about 10% to about 50% or more by weight, and can be selected primarily by fluid volumes, and viscosities, in accordance with the particular mode of administration selected. Further, the amount of inventive anti-mesothelin material in the pharmaceutical formulations can vary, e.g., from less than about 1 µg/ml to greater than about 40 mg/ml, from about 1 µg/ml to about 40 mg/ml, from about 1 µg/ml to about 100 mg/ml, or from less than about 1 µg/ml to greater than about 1000 mg/ml.

Methods for preparing administrable (e.g., parenterally administrable) compositions are known or apparent to those skilled in the art and are described in more detail in, for example, *Remington: The Science and Practice of Pharmacy*, Lippincott Williams & Wilkins; 22nd ed. (2013).

The following formulations for parenteral (e.g., subcutaneous, intravenous, intraarterial, intramuscular, intradermal, intraperitoneal, interperitoneal, and intrathecal) administration are merely exemplary and are in no way limiting. More than one route can be used to administer the inventive anti-mesothelin materials, and in certain instances, a particular route can provide a more immediate and more effective response than another route.

Formulations suitable for parenteral administration include aqueous and nonaqueous isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The inventive anti-mesothelin material can be administered in a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-1,3-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain, for example, from about 0.5% to about 25% by weight of the inventive anti-mesothelin material in solution. Preservatives and buffers may be used. In order to minimize or eliminate irritation at the site of injection, such compositions may contain one or more nonionic surfactants having, for example, a hydrophile-lipophile balance (HLB) of from about 12 to about 17. The quantity of surfactant in such formulations will typically range, for example, from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Injectable formulations are in accordance with an embodiment of the invention. The requirements for effective pharmaceutical carriers for injectable compositions are well-known to those of ordinary skill in the art (see, e.g., *A Practical Guide to Contemporary Pharmacy Practice*, 3rd Edition, Lippincott Williams and Wilkins, Philadelphia, Pa., Thompson and Davidow, eds., (2009), and *Handbook on Injectable Drugs, Trissel*, 16th ed., (2010)).

An "effective amount" or "an amount effective to treat" refers to a dose that is adequate to carry out any one or more of the following: (a) prevent or treat cancer; (b) reduce or prevent TACE activity and (c) reduce mesothelin shed from cell membranes in an individual. Amounts effective for a therapeutic or prophylactic use will depend on, for example, the stage and severity of the disease or disorder being treated, the age, weight, and general state of health of the patient, and the judgment of the prescribing physician. The size of the dose will also be determined by the active selected, method of administration, timing and frequency of administration, the existence, nature, and extent of any adverse side-effects that might accompany the administration of a particular active, and the desired physiological effect. It will be appreciated by one of skill in the art that various diseases or disorders could require prolonged treatment involving multiple administrations, perhaps using the inventive anti-mesothelin materials in each or various rounds of administration. By way of example and not intending to limit the embodiments of the invention, the dose of the inventive anti-mesothelin material can be about 0.001 to about 1000 mg/kg body weight of the subject being treated/day, from about 0.01 to about 10 mg/kg body weight/day, about 0.01 mg to about 1 mg/kg body weight/day.

For purposes of the embodiments of the invention, the amount or dose of the inventive anti-mesothelin material administered should be sufficient to effect a therapeutic or prophylactic response in the subject or animal over a reasonable time frame. For example, the dose of the inventive anti-mesothelin material should be sufficient to bind to mesothelin, reduce mesothelin shed from cell membranes, reduce TACE activity, or detect, treat or prevent cancer in a period of from about 2 hours or longer, e.g., about 12 to about 24 or more hours, from the time of administration. In certain embodiments, the time period could be even longer. The dose will be determined by the efficacy of the particular inventive anti-mesothelin material and the condition of the animal (e.g., human), as well as the body weight of the animal (e.g., human) to be treated.

For purposes of the embodiments of the invention, an assay, which comprises, for example, comparing the extent to which target cells are killed upon administration of a given dose of the inventive anti-mesothelin material to a mammal, among a set of mammals of which is each given a different dose of the inventive anti-mesothelin material, could be used to determine a starting dose to be administered to a mammal. The extent to which target cells are killed upon administration of a certain dose can be assayed by methods known in the art.

The delivery systems useful in the context of embodiments of the invention may include time-released, delayed release, and sustained release delivery systems such that the delivery of the inventive composition occurs prior to, and with sufficient time to cause, sensitization of the site to be treated. The inventive composition can be used in conjunction with other therapeutic agents or therapies. Such systems can avoid repeated administrations of the inventive composition, thereby increasing convenience to the subject and the physician, and may be particularly suitable for certain composition embodiments of the invention.

Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are lipids including sterols such as cholesterol, cholesterol esters, and fatty acids or neutral fats such as mono-di-and tri-glycerides; hydrogel release systems; sylastic systems; peptide based systems; wax coatings; compressed tablets using conventional binders and excipients; partially fused implants; and the like. Specific examples include, but are not limited to: (a)

erosional systems in which the active composition is contained in a form within a matrix and (b) diffusional systems in which an active component permeates at a controlled rate from a polymer. In addition, pump-based hardware delivery systems can be used, some of which are adapted for implantation.

One of ordinary skill in the art will readily appreciate that the inventive anti-mesothelin materials of the invention can be modified in any number of ways, such that the therapeutic or prophylactic efficacy of the inventive anti-mesothelin materials is increased through the modification. For instance, the inventive anti-mesothelin materials can be modified into a depot form, such that the manner in which the inventive anti-mesothelin materials is released into the body to which it is administered is controlled with respect to time and location within the body. Depot forms of inventive anti-mesothelin materials can be, for example, an implantable composition comprising the inventive anti-mesothelin materials and a porous or non-porous material, such as a polymer, wherein the inventive anti-mesothelin materials are encapsulated by or diffused throughout the material and/or degradation of the non-porous material. The depot is then implanted into the desired location within the body and the inventive anti-mesothelin materials are released from the implant at a predetermined rate.

When the inventive anti-mesothelin materials are administered with one or more additional therapeutic agents, one or more additional therapeutic agents can be coadministered to the mammal. By "coadministering" is meant administering one or more additional therapeutic agents and the inventive anti-mesothelin materials sufficiently close in time such that the inventive anti-mesothelin materials can enhance the effect of one or more additional therapeutic agents, or vice versa. In this regard, the inventive anti-mesothelin materials can be administered first and the one or more additional therapeutic agents can be administered second, or vice versa. Alternatively, the inventive anti-mesothelin materials and the one or more additional therapeutic agents can be administered simultaneously.

It is contemplated that the inventive anti-mesothelin materials and pharmaceutical compositions can be used in methods of treating or preventing cancer in a mammal. Without being bound to a particular theory or mechanism, the inventive anti-mesothelin materials have biological activity, e.g., ability to recognize antigen, e.g., mesothelin, such that the anti-mesothelin material, can direct an effector molecule to a target cell or target tissue. In this regard, an embodiment of the invention provides a method of treating or preventing cancer, comprising administering to the mammal any of the polypeptides, proteins, functional portions, functional variants, nucleic acids, recombinant expression vectors, host cells, population of cells, anti-mesothelin binding moieties, conjugates, and/or the pharmaceutical compositions in an amount effective to treat or prevent cancer.

An embodiment of the invention further comprises lymphodepleting the mammal prior to administering the inventive anti-mesothelin materials. Examples of lymphodepletion include, but may not be limited to, nonmyeloablative lymphodepleting chemotherapy, myeloablative lymphodepleting chemotherapy, total body irradiation, etc.

The mammal referred to herein can be any mammal. As used herein, the term "mammal" refers to any mammal, including, but not limited to, mammals of the order Rodentia, such as mice and hamsters, and mammals of the order Logomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes). Preferably, the mammal is a human.

With respect to the inventive methods, the cancer can be any cancer, including any of acute lymphocytic cancer, acute myeloid leukemia, rhabdomyosarcoma, bladder cancer (e.g., bladder carcinoma), bone cancer, brain cancer (e.g., medulloblastoma, neuroblastoma, and glioblastoma), breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the ovary, vulva, endometrium, or chronic lymphocytic leukemia, chronic myeloid cancer, colon cancer, Ewing's sarcoma, esophageal cancer, cervical cancer, fibrosarcoma, gastrointestinal carcinoid tumor, head and neck cancer (e.g., head and neck squamous cell carcinoma), Hodgkin lymphoma, hypopharynx cancer, kidney cancer, larynx cancer, leukemia, liquid tumors, liver cancer, lung cancer (e.g., non-small cell lung carcinoma, lung adenocarcinoma), lymphoma, malignant mesothelioma, mastocytoma, melanoma, multiple myeloma, nasopharynx cancer, neuroblastoma, non-Hodgkin lymphoma, B-chronic lymphocytic leukemia, hairy cell leukemia, acute lymphocytic leukemia (ALL), and Burkitt's lymphoma, ovarian cancer, pancreatic cancer, gastric cancer, peritoneum, omentum, and mesentery cancer, pharynx cancer, prostate cancer, rectal cancer, renal cancer, skin cancer, small intestine cancer, soft tissue cancer, solid tumors, stomach cancer, testicular cancer, thyroid cancer, synovial cancer, and ureter cancer. Preferably, the cancer is ovarian cancer, endometrial cancer, cervical cancer, colonic cancer, pancreatic cancer, lung cancer (e.g., non-small cell lung carcinoma, lung adenocarcinoma), esophageal cancer, gastric cancer, synovial sarcoma, and mesothelioma. In an embodiment, the cancer is characterized by the expression or overexpression of mesothelin.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

Another embodiment of the invention provides a kit for treating or preventing cancer, the kit comprising any of the polypeptides, proteins, anti-mesothelin binding moieties, conjugates, nucleic acids, recombinant expression vectors, isolated host cells, populations of cells, or pharmaceutical compositions described herein with respect to other aspects of the invention. In an embodiment of the invention, the kit may further comprise any one or more of (a) pharmaceutically acceptable carrier(s) as described herein with respect to other aspects of the invention (e.g., buffering agent(s)); (b) printed instructions for using the kit; (c) one or more other pharmaceutically active agent(s) or drug(s), such as chemotherapeutic agent(s), as described herein with respect to other aspects of the invention. The printed instructions for using the kit may recite methods of administering the inventive anti-mesothelin material(s) as described herein with respect to other aspects of the invention. In an embodiment of the invention, the kit further comprises separate containers for holding each of the one or more pharmaceutically acceptable carrier(s), each of the one or more inventive anti-mesothelin material(s), and each of the one or more other pharmaceutically active agent(s) or drug(s).

Another embodiment of the invention provides any of the polypeptides, proteins, functional portions, functional variants, nucleic acids, recombinant expression vectors, host cells, population of cells, anti-mesothelin binding moieties, conjugates, or pharmaceutical compositions of the invention for use in a method of treating or preventing cancer.

Another embodiment of the invention provides a method of detecting the presence of cancer in a mammal comprising: (a) contacting a sample comprising one or more cells from the mammal with any of the polypeptides, proteins, functional portions, functional variants, nucleic acids, recombinant expression vectors, host cells, population of cells, anti-mesothelin binding moieties, or conjugates, thereby forming a complex, (b) and detecting the complex, wherein detection of the complex is indicative of the presence of cancer in the mammal.

The sample may be obtained by any suitable method, e.g., biopsy or necropsy. A biopsy is the removal of tissue and/or cells from an individual. Such removal may be to collect tissue and/or cells from the individual in order to perform experimentation on the removed tissue and/or cells. This experimentation may include experiments to determine if the individual has and/or is suffering from a certain condition or disease-state. The condition or disease may be, e.g., cancer.

With respect to an embodiment of the inventive method of detecting the presence of cancer in a mammal, the sample comprising cells of the mammal can be a sample comprising whole cells, lysates thereof, or a fraction of the whole cell lysates, e.g., a nuclear or cytoplasmic fraction, a whole protein fraction, or a nucleic acid fraction. If the sample comprises whole cells, the cells can be any cells of the mammal, e.g., the cells of any organ or tissue, including blood cells or endothelial cells.

For purposes of the inventive detecting method, the contacting can take place in vitro or in vivo with respect to the mammal. Preferably, the contacting is in vitro.

Also, detection of the complex can occur through any number of ways known in the art. For instance, the inventive polypeptides, proteins, functional portions, functional variants, nucleic acids, recombinant expression vectors, host cells, populations of cells, anti-mesothelin binding moieties, or conjugates, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

Methods of testing an anti-mesothelin material for the ability to recognize target cells and for antigen specificity are known in the art. For instance, Clay et al., *J. Immunol.,* 163: 507-513 (1999), teaches methods of measuring the release of cytokines (e.g., interferon-γ, granulocyte/monocyte colony stimulating factor (GM-CSF), tumor necrosis factor a (TNF-α) or interleukin 2 (IL-2)). In addition, anti-mesothelin material function can be evaluated by measurement of cellular cytotoxicity, as described in Zhao et al., *J. Immunol.,* 174: 4415-4423 (2005).

Another embodiment of the invention provides a method of reducing mesothelin shed from cell membranes, the method comprising administering to cells any of the inventive polypeptides, proteins, anti-mesothelin binding moieties, conjugates, nucleic acids, recombinant expression vectors, host cells, population of cells, or the pharmaceutical compositions described herein, in an amount effective to reduce mesothelin shed from the cell membranes of the cells.

As used herein, "reducing mesothelin shed from cell membranes" means a reduction in the quantity of mesothelin protein, or portion thereof, removed from a cell following administration of one or more of the inventive anti-mesothelin materials compared to the quantity that would have been removed from the cell without the administration of the inventive anti-mesothelin material(s) to the cells.

Another embodiment of the invention provides a method of reducing the activity of TNFα converting enzyme in a mammal, the method comprising administering to the mammal any of the polypeptides, proteins, anti-mesothelin binding moieties, conjugates, nucleic acids, recombinant expression vectors, host cells, population of cells, or the pharmaceutical compositions of the embodiments of the present invention, in an amount effective to reduce the activity of TNFα converting enzyme in the mammal.

As used herein, "reducing the activity of TNFα converting enzyme" means a reduction in the biological activity of TACE following administration of one or more of the inventive anti-mesothelin materials as compared to the biological activity of TACE without the administration of the inventive anti-mesothelin material(s) to the mammal. The biological activity of TACE may include, for example, TACE-mediated cleavage of mesothelin protein, or portion thereof, from a cell.

The following examples further illustrate the invention but, of course, should not be construed as in any way limiting its scope.

EXAMPLE 1

This example demonstrates that the inventive antibodies bind to mesothelin IPNGYLVLDLSMQEALS (SEQ ID NO: 1).

The amino acid sequences (peptides) that remain associated with the cell membrane when mesothelin is shed were determined to be: 587-LVLDLSMQEALS-598 (SEQ ID NO: 58) and 592-SMQEALS-598 (SEQ ID NO: 60). The S-598 is attached to phosphatidyl inositol.

To make antibodies to the region of mesothelin that is left behind when mesothelin is released and also to the TACE cutting sites, a peptide C-582-IPNGYLVLDLSMQEALS-598 (SEQ ID NO: 1) was made. This peptide contains the amino acids that are positioned close to the membrane as well as the amino acids making up the TACE cleavage sites. A cysteine was added at the amino terminus to allow conjugation to carrier proteins used for immunization of mice.

A keyhole limpet hemocyanin ("KLH")-peptide conjugate was prepared and used to immunize Balb/C mice. The mice developed antibodies which reacted with native human mesothelin, indicating that the anti-peptide antibodies also recognize native human mesothelin.

Hybridomas were made from spleen cells of these mice, and clones were isolated that produced antibodies that reacted by enzyme-linked immunosorbent assay ("ELISA") with Fc-mesothelin 296-599. The sequences of the Fv regions of the antibodies and the hybridomas produced are shown in Table 1. These antibodies are 15B6 (IgG 2b), 2B4 (IgG 2a), and 7B5 (IgG 1).

TABLE 1

| Sequence | Antibody | Region |
|---|---|---|
| GHYMH (SEQ ID NO: 2) | 2B4 (IgG2a) | VH CDR1 |
| RINPYTGAINYNQNFKD (SEQ ID NO: 3) | 2B4 (IgG2a) | VH CDR2 |
| DLGGGY (SEQ ID NO: 4) | 2B4 (IgG2a) | VH CDR3 |
| RSSTGAVTTSNYAN (SEQ ID NO: 5) | 2B4 (IgG2a) | VL CDR1 |
| GTNNRAP (SEQ ID NO: 6) | 2B4 (IgG2a) | VL CDR2 |
| ALWYSSHWV (SEQ ID NO: 7) | 2B4 (IgG2a) | VL CDR3 |
| GHYMH (SEQ ID NO: 8) | 7B5 (IgG1) | VH CDR1 |
| RINPYTGAINYNQNFKD (SEQ ID NO: 9) | 7B5 (IgG1) | VH CDR2 |
| DLGGGY (SEQ ID NO: 10) | 7B5 (IgG1) | VH CDR3 |
| RSSTGAVTTSNYAN (SEQ ID NO: 11) | 7B5 (IgG1) | VL CDR1 |
| GTNNRAP (SEQ ID NO: 12) | 7B5 (IgG1) | VL CDR2 |
| ALWFGSHWV (SEQ ID NO: 13) | 7B5 (IgG1) | VL CDR3 |
| GYYMH (SEQ ID NO: 14) | 15B6 (IgG2b) | VH CDR1 |
| RINPYTGVPSYKHNFKD (SEQ ID NO: 15) | 15B6 (IgG2b) | VH CDR2 |
| ELGGY (SEQ ID NO: 16) | 15B6 (IgG2b) | VH CDR3 |
| RSSTGAVTTGNYPN (SEQ ID NO: 17) | 15B6 (IgG2b) | VL CDR1 |
| GTNNRAP (SEQ ID NO: 18) | 15B6 (IgG2b) | VL CDR2 |
| ALWFSSHWV (SEQ ID NO: 19) | 15B6 (IgG2b) | VL CDR3 |
| EVQLQQSGPELVKPGASVKISCKASGYPFTGHYM HWVKQGHVKSLEWIGRINPYTGAINYNQNFKDKA SLSVEKSSSTAYMGLHSLTSEDSAVYYCVRDLGGG YWGQGTTLTVSS (SEQ ID NO: 20) | 2B4 (IgG2a) | VH |
| QAVVTQESALTTSPGETVTLTCRSSTGAVTTSNY ANWVQEKPDHLFTGLIAGTNNRAPGVPARFSGSLIG DKAALTITGAQPEDEAIFFCALWYSSHW VFGGGTKLTVL (SEQ ID NO: 21) | 2B4 (IgG2a) | VL |
| EVQLQQSGPELVKPGTSVKISCKASGYPFTGHYMHW VKQGHVKSLEWIGRINPYTGAINYNQNFKDKASLTV EKSSSTAYMGLHSLTSEDSAVYYCVRDLGGGYWGQ GTTLTVSS (SEQ ID NO: 22) | 7B5 (IgG1) | VH |
| QAVVTQESALTTSPGETVTLTCRSSTGAVT TSNYANWVQEKPDHLFTG LIAGTNNRAPGV PARFSGSLIGDKAALTITGAQPEDEAMFFCAL WFGSHWVFGGGTKLTVL (SEQ ID NO: 23) | 7B5 (IgG1) | VL |
| EVQLQQSGPVLVKPGASVKISCKASGYSFTGY YMHWVRQSLVKRLEWIGRINPYTGVPSYKHNF KDKASLTVDKSSSTAYMELHSLTSEDSAVYYCA RELGGYWGQGTTLTVSS (SEQ ID NO: 24) | 15B6 (IgG2b) | VH |
| QAVVTQESALTTSPGETVTLTCRSSTGAVTTGNYPN WVQEKPDHLFTGLIAGTNNRAPGVPARFSGSLIGDK AALTITGAQTEDEAIYFCALWFSSHWVFGGGTKLTVL (SEQ ID NO: 25) | 15B6 (IgG2b) | VL |

EXAMPLE 2

This example demonstrates that the antibodies of Example 1 bind to mesothelin on A431/M cells.

Binding assays were conducted with A431/M cells using FACS. A431/MSLN(M) cells were transfected with a MSLN(M) expression plasmid. Cells ($10^6$) were incubated with monoclonal antibodies at concentrations ranging from 0.01 to 100 ng/ml for one hour. After the cells were washed, anti-mouse IgG-PE conjugates were added. The PE signal was detected and measured in Geometric Mean values by FACS. The results are shown in FIG. 1 and indicate that the 2B4, 7B5, and 15B6 antibodies of Example 1 bind mesothelin on A431/M.

EXAMPLE 3

This example demonstrates that the antibodies of Example 1 are specific for the carboxyl (C) terminus of mesothelin.

The monoclonal antibodies of Example 1 were also tested for binding to the AB1-L9 cell line, which was transfected with a plasmid encoding a portion of mesothelin (MSLN) attached to a mouse transferrin receptor ("TFR") membrane spanning region and is missing the sequences in the peptide used for making the hybridomas. This transfected gene contains mesothelin (296-585) attached to TFR transmembrane domain LCFAAIALVIFFLIGFMSGYLGYG (SEQ ID NO: 64). Although the expression of mesothelin in transfected cells was confirmed by MN (control) antibody, none of the monoclonal antibodies bound to the AB1-L9 cell, indicating that they are specific for the C terminus of mesothelin (residues 584-598). These data indicate that the antibodies of Example 1 are specific for the C terminus of mesothelin.

EXAMPLE 4

This example demonstrates that the 15B6 antibody of Example 1 strongly binds to cancer cell lines known to express mesothelin.

The monoclonal 15B6 antibodies of Example 1 were tested for binding to cell lines KLM-1 (pancreatic cancer cell line), RH29 (mesothelioma), and A431/M, a cell line transfected with a mesothelin variant with M at position 593. $10^6$ cells of A431/M were incubated with the 15B6 antibodies of Example 1 at concentrations ranging from 1 to 10,000 ng/ml for one hour. $10^6$ cells of RH29 were incubated with the 15B6 antibodies of Example 1 at concentrations ranging from 0.001 to 10 ug/ml for one hour. $10^6$ cells of KLM-1 were incubated with the antibodies of Example 1 at concentrations ranging from 1 to 10,000 ng/ml for one hour. After washing the cells, anti-mouse IgG-PE conjugate was added.

Figure 2:
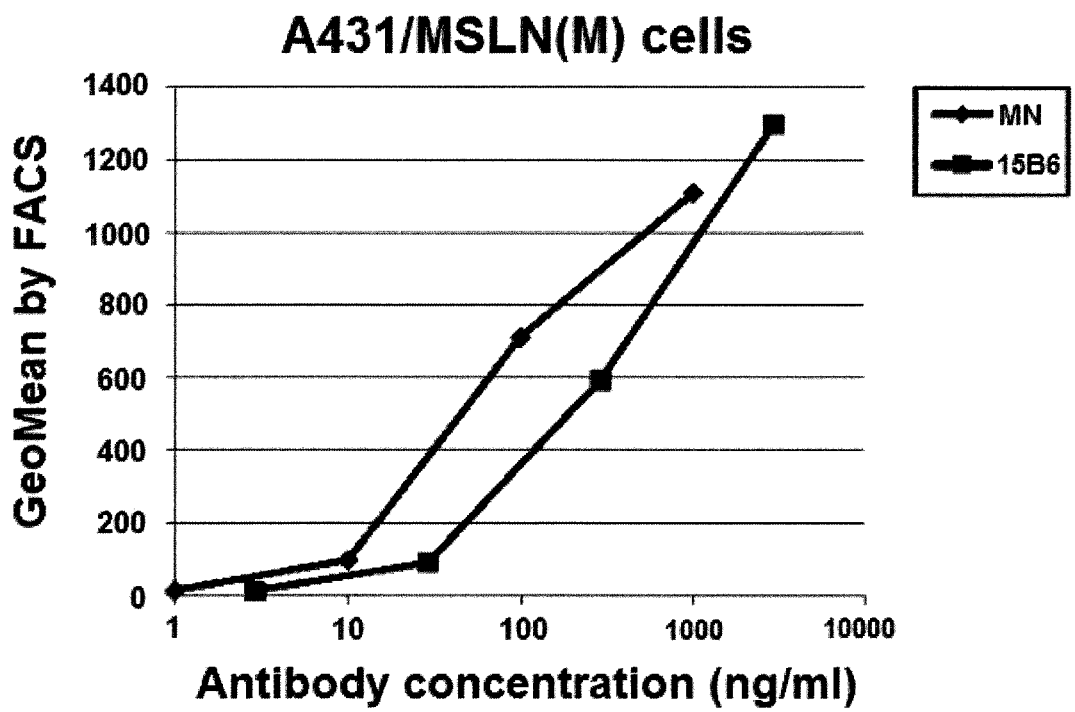
FIG. 2 is a graph showing binding of antibodies to A431/MSLN(M) cells measured (GeoMean) by FACS.

FIG. 2 shows that antibody 15B6 bound strongly to A431/MSLN(M) cells compared to the control antibody MN.

Figure 3:
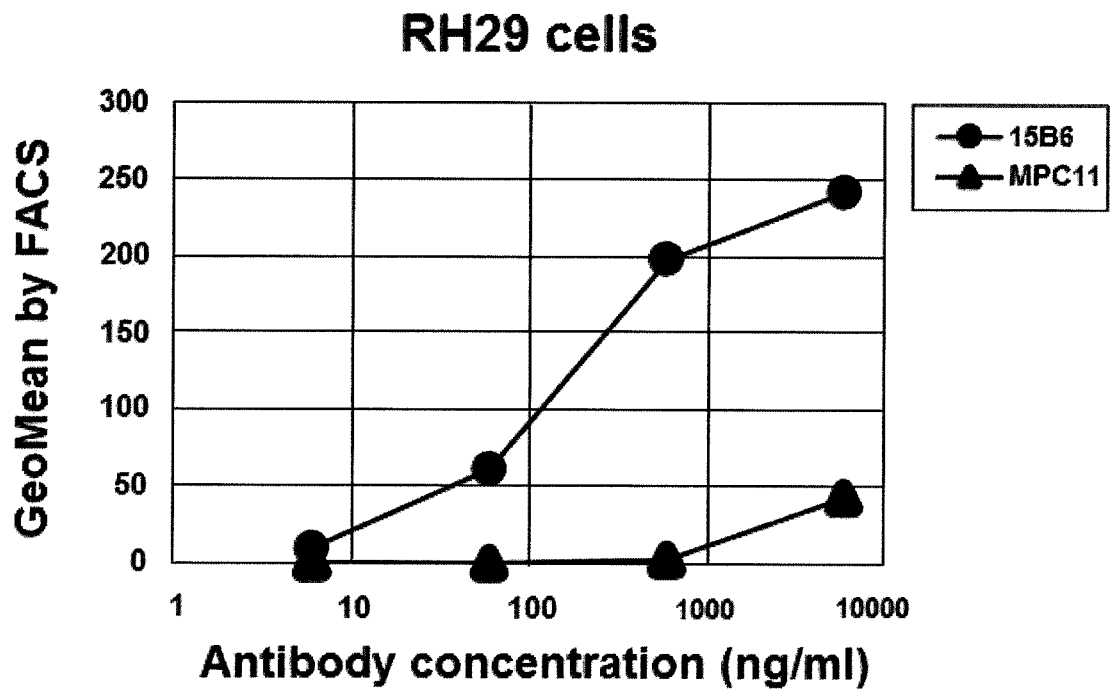
FIG. 3 is a graph showing binding of antibodies to RH29 (mesothelioma cell line) measured (GeoMean) by FACS.

FIG. 3 shows that antibody 15B6 bound strongly to RH29 cells compared to the control antibody MPC11.

Figure 4:
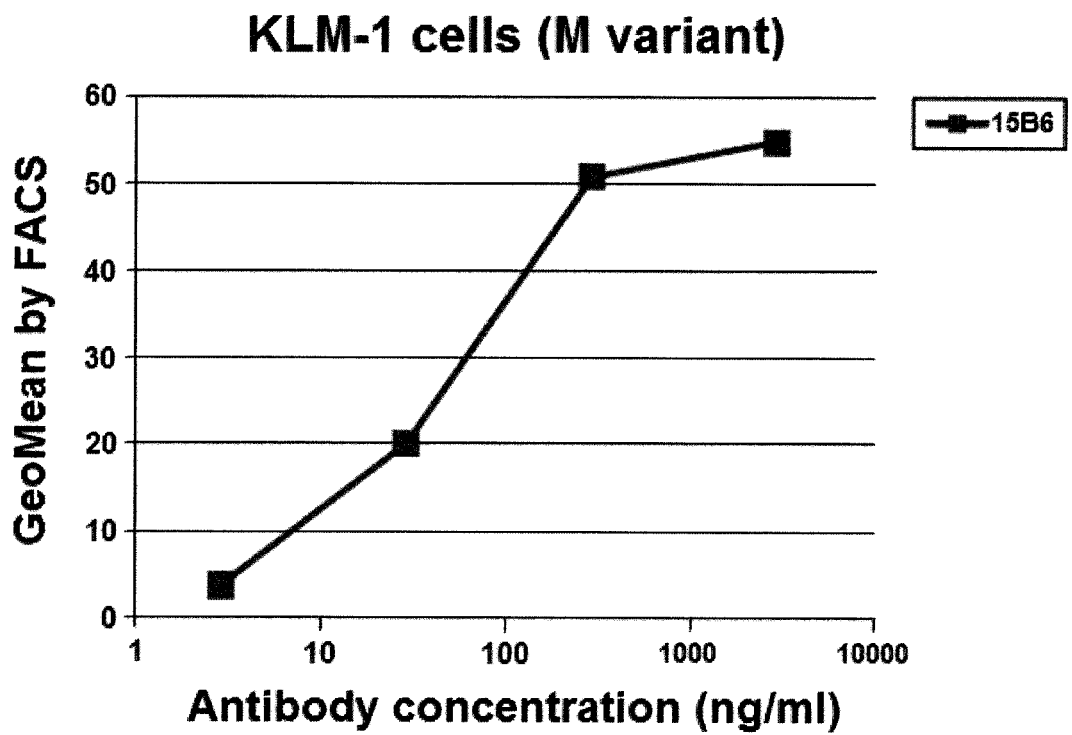
FIG. 4 is a graph showing the binding of Mab 15B6 to KLM-1 cells (pancreatic cancer cell line) measured (GeoMean) by FACS.

FIG. 4 shows that antibody 15B6 bound strongly to KLM-1 cells (M variant).

EXAMPLE 5

This example demonstrates that the 15B6 antibody of Example 1 binds to MSLN(M)-rFc.

Figure 5:
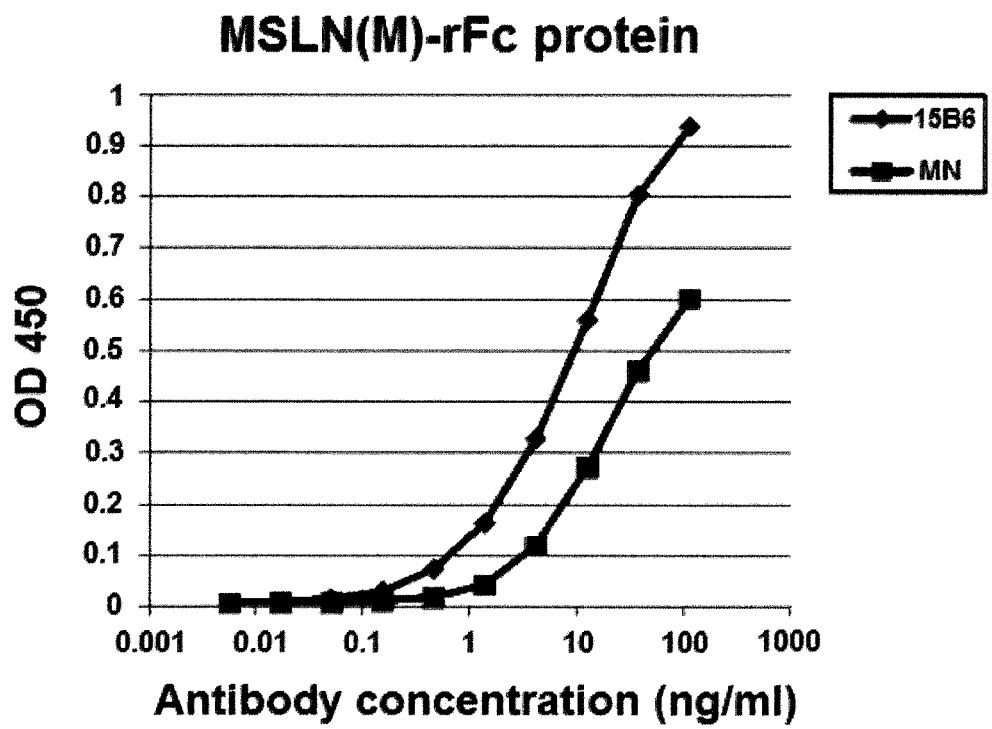
FIG. 5 is a graph showing the optical density ("OD") reading at 450 nm as measured in an ELISA binding assay for MSLN(M)-Fc after being incubated with antibody 15B6 (comprising SEQ ID NOs: 14-19) (diamonds) or control antibody MN (squares).

One microgram per milliliter of MSLN(M)-rFc protein was coated on an ELISA plate. After overnight incubation, concentrations of antibody 15B6 ranging from less than 0.1 to 100 ng/ml were added. The amount of bound 15B6 was detected with anti-mouse IgG-HRP conjugates. 3,3',5,5'-Tetramethylbenzidine ("TMB") substrate was added and the OD 450 was determined with a micro plate reader. MN was used as the control antibody. The ELISA results are shown in FIG. 5 and indicate that the 15B6 antibody of Example 1 binds to MSLN(M)-rFc.

EXAMPLE 6

This example demonstrates that the 15B6 antibody of Example 1 binds to MSLN(V)-rFc.

Figure 6:
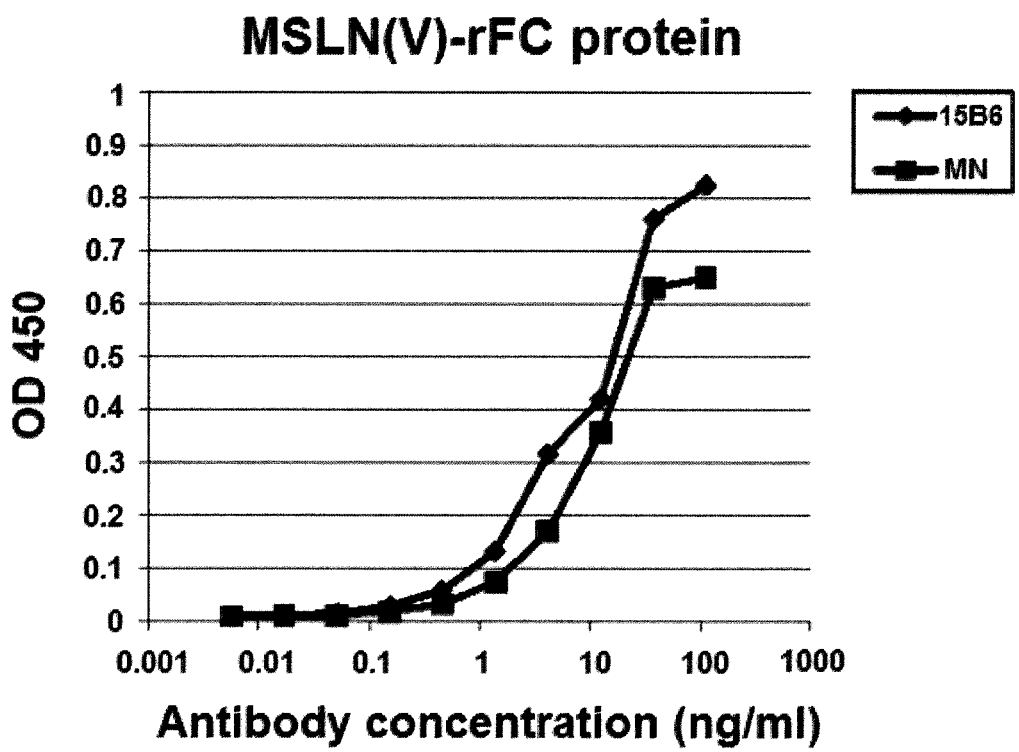
FIG. 6 is a graph showing the OD reading at 450 nm as measured in an ELISA binding assay for MSLN(V)-Fc after being incubated with antibody 15B6 (comprising SEQ ID NOs: 14-19) (diamonds) or control antibody MN (squares).

One microgram per milliliter of MSLN(V)-rFc protein was coated on an ELISA plate. After overnight incubation, concentrations of antibody 15B6 ranging from less than 0.1 to 100 ng/ml were added. The amount of bound 15B6 was detected with anti-mouse IgG-HRP conjugates. TMB substrate was added and the OD 450 was determined with a micro plate reader. MN was used as the control antibody. The ELISA results are shown in FIG. 6 and indicate that the 15B6 antibody of Example 1 binds to MSLN(V)-rFc.

EXAMPLE 7

This example demonstrates that the 15B6 antibody of Example 1 dramatically reduces mesothelin shedding.

Figure 7:
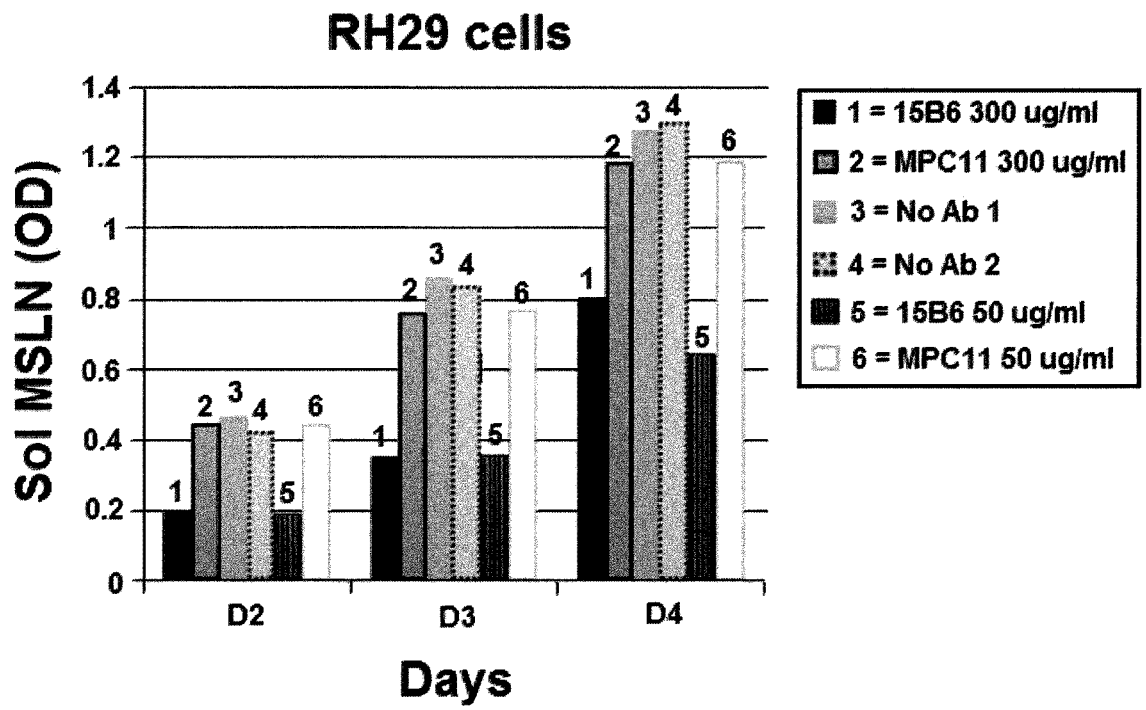
FIG. 7 is a graph showing the amount of soluble mesothelin released by RH29 cells as measured in a sandwich ELISA as quantitative assay. Antibody 15B6 (comprising SEQ ID NOs: 14-19) reduced mesothelin shedding by 50% (OD value) at concentrations of 50 and 300 microgram/ml in RH29 cells. Levels of antibody 15B6 (comprising SEQ ID NOs: 14-19) at 300 microgram/ml (black bar (1)), control antibody MPC11 at 300 microgram/ml (grey bar with solid black outline (2)), no antibody (grey bar (3)), no antibody 2 (light grey bar with dotted outline (4)), antibody 15B6 (comprising SEQ ID NOs: 14-19) at 50 microgram/ml (vertical striped bar (5)), and control antibody MPC11 at 50 microgram/ml (lightest grey bar with solid grey outline (6)) were determined at days 2, 3, and 4 (D2, D3, and D4, respectively).

RH29 mesothelioma cells ($3.5 \times 10^5$) were incubated with various amounts of antibody (300 ug/ml or 50 ug/ml) for 2-4 days and the amount of mesothelin shed in the medium was measured by ELISA. MPC11 antibody was used as the control. Samples were taken on days 2, 3, and 4 (shown in FIGS. 7 as D2, D3, and D4, respectively). As seen in FIG. 7, antibody 15B6 reduced mesothelin shedding by 50% (OD value) at concentrations of 50 and 300 microgram/ml of antibody. This study indicates that antibody the 15B6 antibody of Example 1 binds to or near the TACE cutting site and prevents TACE from releasing mesothelin.

EXAMPLE 8

This example demonstrates that the antibodies of Example 1 compete with LVLDL peptide (SEQ ID NO: 63).

A competition assay was completed using the following peptides: peptide 1 having the sequence CLVLD-LSMQEALS (SEQ ID NO: 61) and peptide 2 having the sequence CSMQEALS (SEQ ID NO: 62). An ELISA plate was coated with MSLN(M)-Fc or MSLN(V)-Fc. After overnight incubation, the plates were blocked and washed. The anti-mesothelin stalk antibodies of Example 1 (30 ng/ml) and peptide 1 or peptide 2 were added at different concentrations (100 micrograms/ml to 0.00001 micrograms/ml). After washing, anti-mouse IgG-HRP conjugate were added. The OD was then measured with ELISA.

Figure 8:
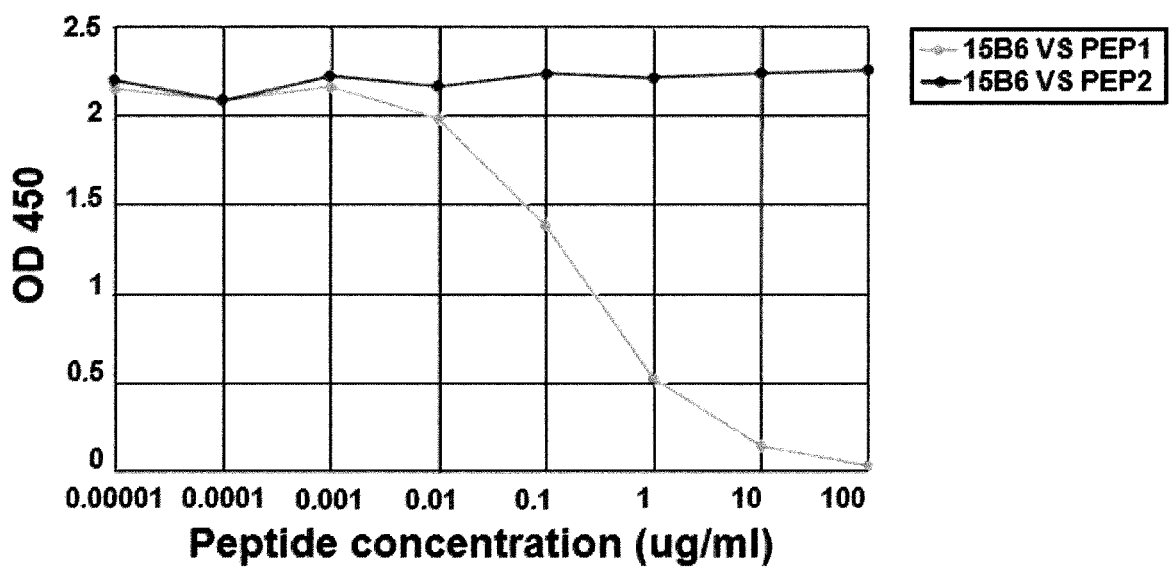
FIG. 8 is a graph showing binding of 30 ng/ml of 15B6 antibody (comprising SEQ ID NOs: 14-19) to MSLN(M)-Fc antigen by ELISA, as incubated with competitor peptide 1 (SEQ ID NO: 61) and peptide 2 (SEQ ID NO: 62).
Figure 9:
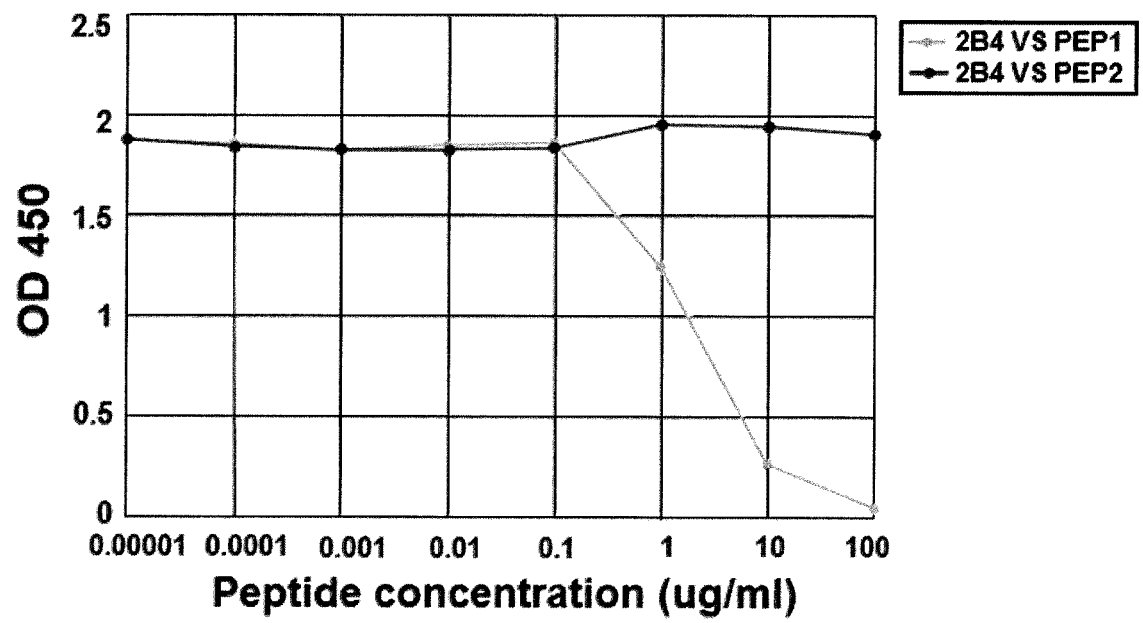
FIG. 9 is a graph showing binding of 30 ng/ml of antibody 2B4 (comprising SEQ ID NOs: 2-7) to MSLN(M)-Fc antigen by ELISA, as incubated with competitor peptide 1 (SEQ ID NO: 61) and peptide 2 (SEQ ID NO: 62).
Figure 10:
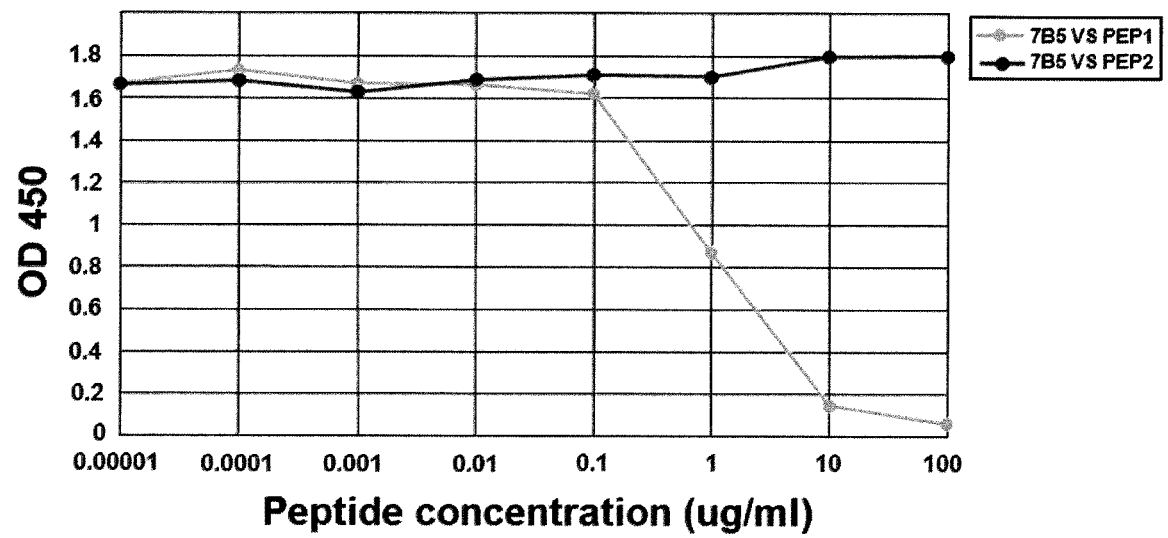
FIG. 10 is a graph showing binding of 30 ng/ml of antibody 7B5 (comprising SEQ ID NOs: 8-13) to MSLN (M)-Fc antigen by ELISA, as incubated with competitor peptide 1 (SEQ ID NO: 61) and peptide 2 (SEQ ID NO: 62).
Figure 11:
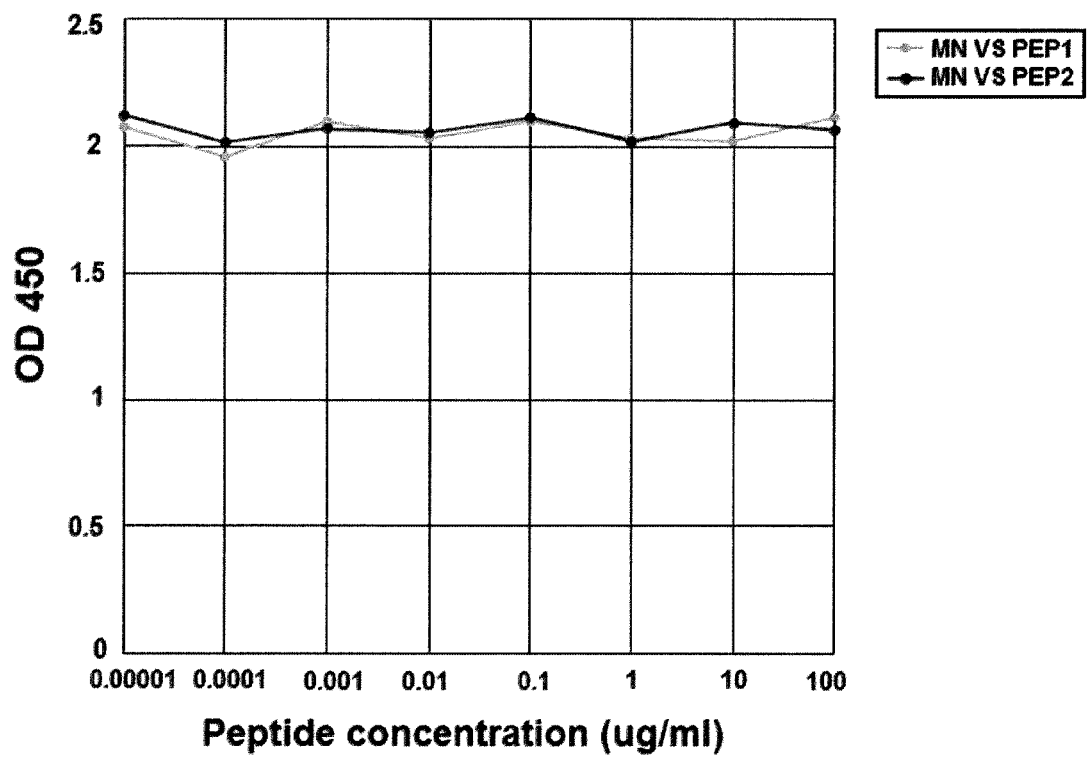
FIG. 11 is a graph showing binding of 30 ng/ml of antibody MN to MSLN(M)-Fc antigen by ELISA, as incubated with competitor peptide 1 (SEQ ID NO: 61) and peptide 2 (SEQ ID NO: 62). This was a control experiment for FIGS. 8-10.

The antibodies of Example 1 competed with peptide 1 but not peptide 2, which indicates that 587-LVLDL-591 (SEQ ID NO: 63) provides strong binding, although the other residues of IPNGYLVLDLSMQEALS could contribute to binding (see FIGS. 8-10). The control antibody (MN) did not compete with either peptide because MN's epitope is on the N-terminus of mesothelin (see FIG. 11).

EXAMPLE 9

This example demonstrates that the antibodies of Example 1 reduce mesothelin shedding.

Figure 12:
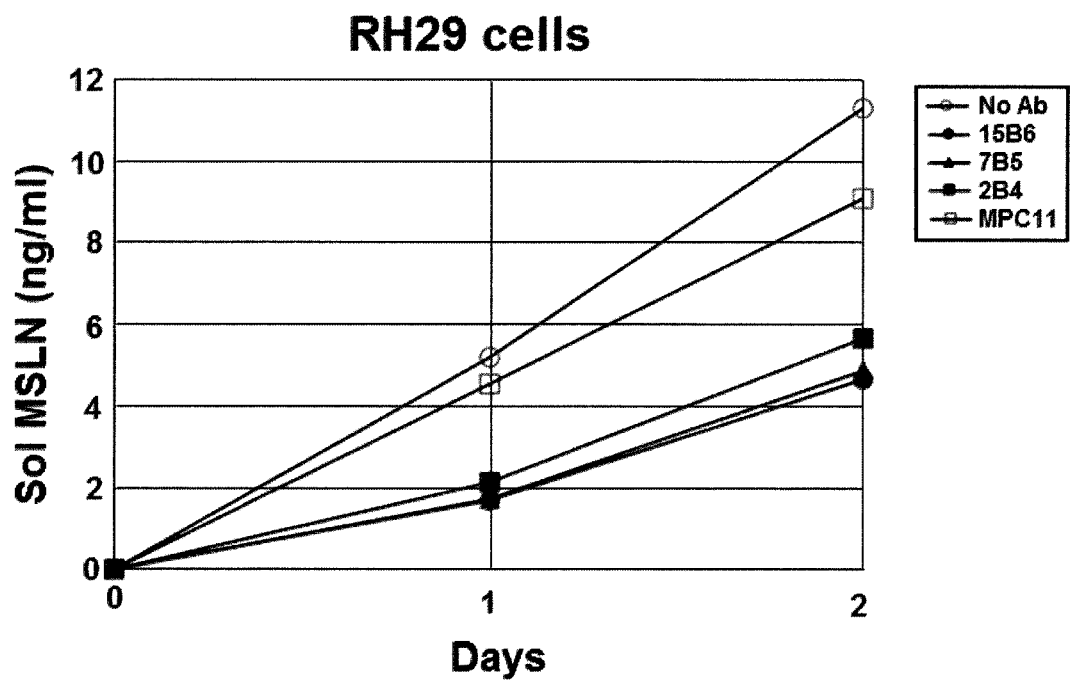
FIG. 12 is a graph showing the amount of shed soluble mesothelin (in nanograms/ml) released by RH29 cells as measured in an quantitative sandwich ELISA assay at time points (days) for no antibody (open circles), control antibody MPC11 (open squares), antibody 2B4 (comprising SEQ ID NOs: 2-7) (closed squares), antibody 7B5 (comprising SEQ ID NOs: 8-13) (triangles), and antibody 15B6 (comprising SEQ ID NOs: 14-19) (closed circles).
Figure 13:
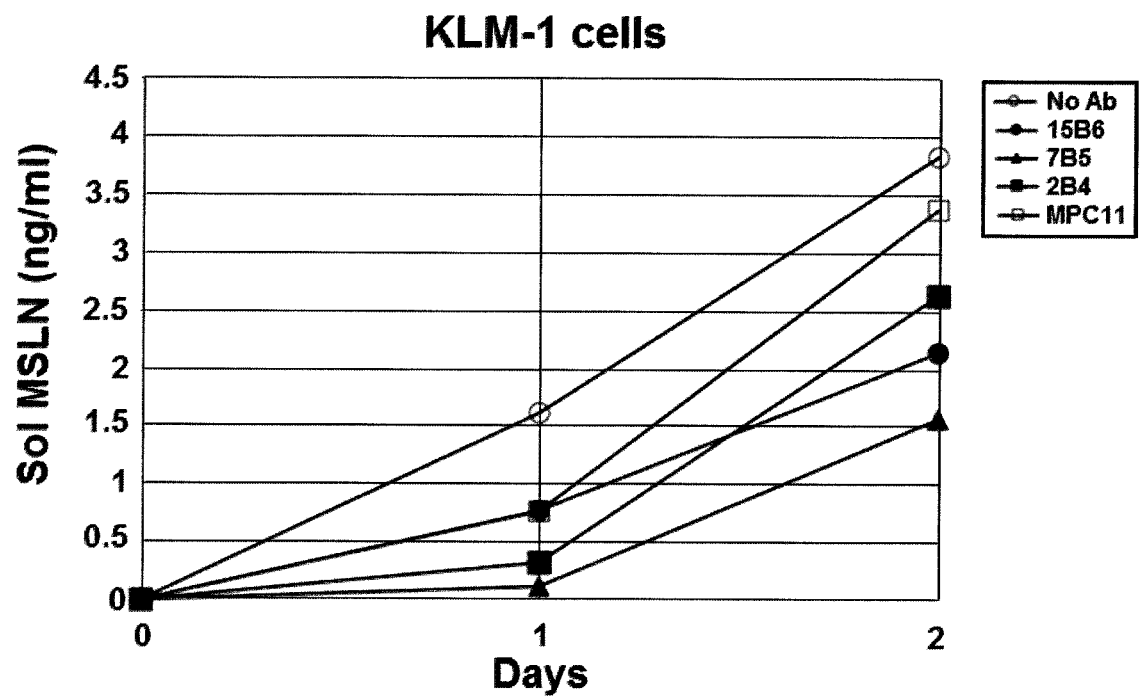
FIG. 13 is a graph showing the amount of shed soluble mesothelin (in nanograms/ml) released by KLM-1 cells as measured in an quantitative sandwich ELISA assay at time points (days) for no antibody (open circles), control antibody MPC11 (open squares), antibody 2B4 (comprising SEQ ID NOs: 2-7) (closed squares), antibody 7B5 (comprising SEQ ID NOs: 8-13) (triangles), and antibody 15B6 (comprising SEQ ID NOs: 14-19) (closed circles).

The monoclonal antibodies were tested for their ability to reduce the shedding of mesothelin by cell line KLM-1 (100% M variant) and RH29 (V and M variant ratio 50:50). The cells ($3 \times 10^5$ cells) on Day -1 were placed in a 6 well plate in medium (2 ml). On Day 0 the medium was removed and 2 ml of fresh medium was added with or without the antibodies of the present invention (50 micrograms/ml). One hundred microliters of supernatant was removed on Days 1, 2, and 3 and the soluble mesothelin amount was determined by ELISA. As seen in FIGS. 12 and 13, the antibodies inhibited mesothelin shedding. Antibody 15B6 reacted with M and V variants while 7B5 and 2B4 reacted with the M variant only. FIG. 12 shows the amount of shed soluble mesothelin released by RH29 with or without antibodies and FIG. 13 shows the amount of shed soluble mesothelin released by KLM-1 with or without antibodies.

EXAMPLE 10

This example demonstrates that antibodies of Example 1 bind to MSLN(V)-rFc and MSLN(M)-rFc variants.

Figure 14:
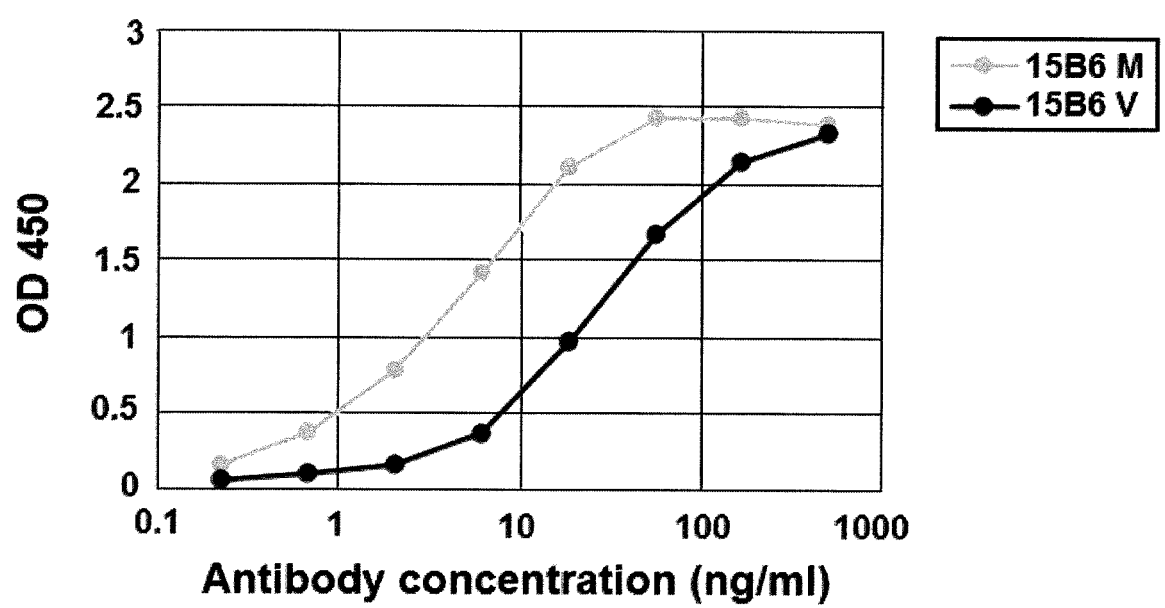
FIG. 14 is a graph showing binding of antibody 15B6 (comprising SEQ ID NOs: 14-19 at the indicated concentrations) to MSLN(M)-Fc (gray line) or MSLN(V)-Fc (black line) measured by ELISA.
Figure 15:
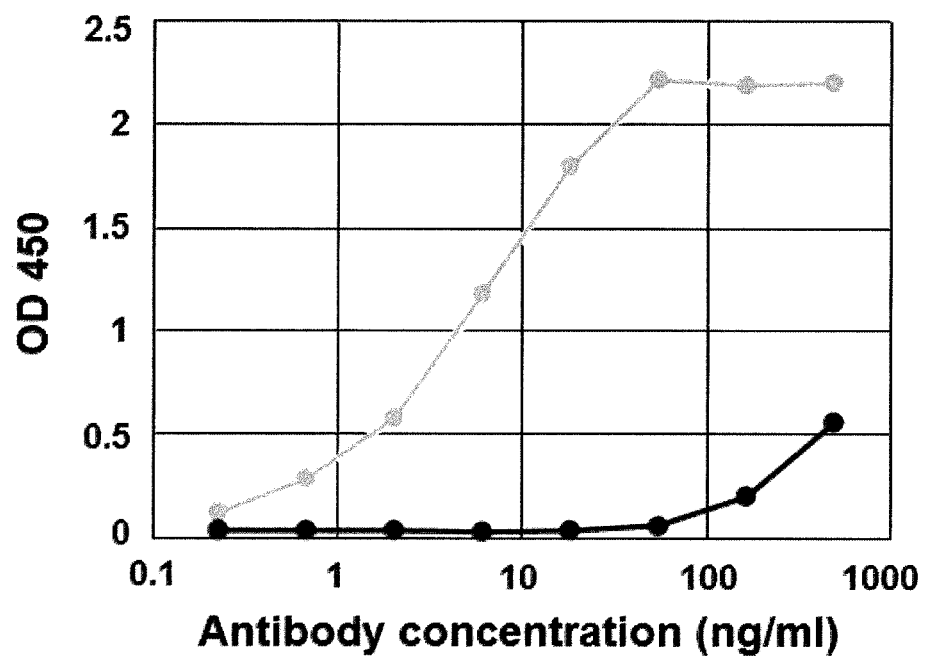
FIG. 15 is a graph showing binding of antibody 2B4 (comprising SEQ ID NOs: 2-7 at the indicated concentrations) to MSLN(M)-Fc (gray line) or MSLN(V)-Fc (black line) measured by ELISA.
Figure 16:
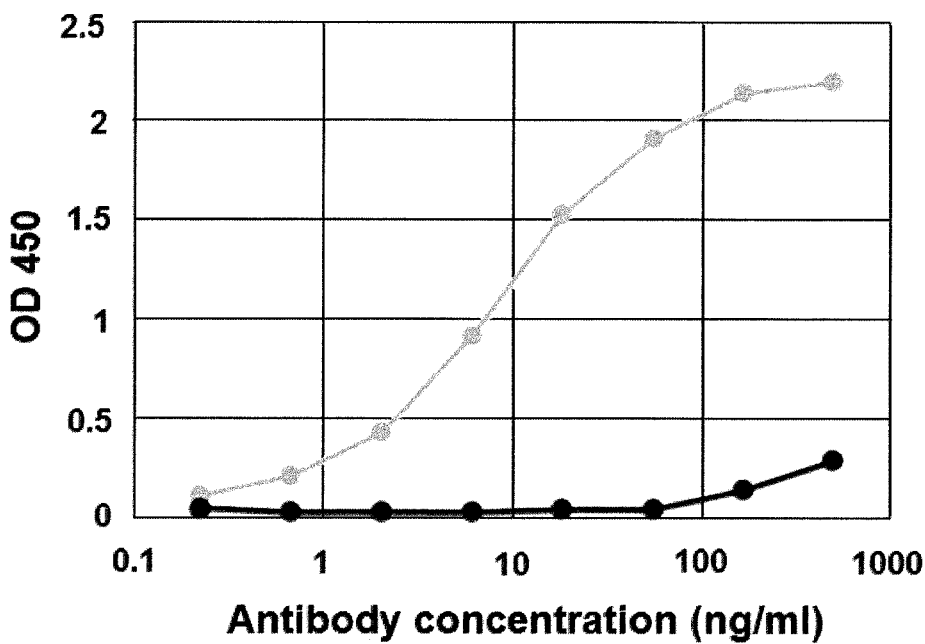
FIG. 16 is a graph showing binding of antibody 7B5 (comprising SEQ ID NOs: 8-13 at the indicated concentrations) to MSLN(M)-Fc (gray line) or MSLN(V)-Fc (black line) measured by ELISA.
Figure 17:
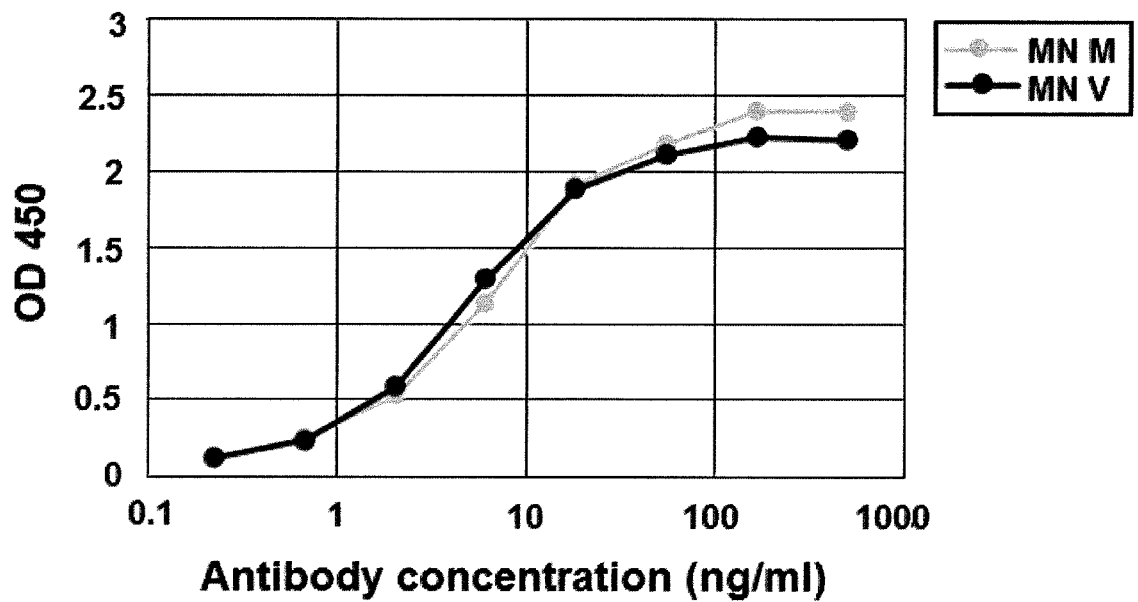
FIG. 17 is a graph showing binding of antibody MN to MSLN(M)-Fc (gray line) or MSLN(V)-Fc (black line) measured by ELISA. This was a control experiment for FIGS. 15-18.

An ELISA plate was coated with variants MSLN(M)-Fc or MSLN(V)-Fc. After washing, antibodies 15B6, 2B4, and 7B5 were added at concentrations ranging from less than 1 to more than 100 ng/ml. The amount of bound antibody was detected using anti-mouse IgG-horseradish peroxidase ("HRP"). FIG. 14 shows the results from a second screening of 15B6 while FIGS. 15-17 show the results of a first screening of these antibodies. MN was used as the control and it binds to both M and V variants (FIG. 17). This assay shows that 15B6 successfully binds to both M and V variants (see FIG. 14), while 2B4 (FIGS. 15) and 7B5 (FIG. 16) only bind to the M variant.

EXAMPLE 11

This example relates to the RH29 cell growth inhibition attributable to 15B6 antibodies of Example 1 observed.

Figure 18:
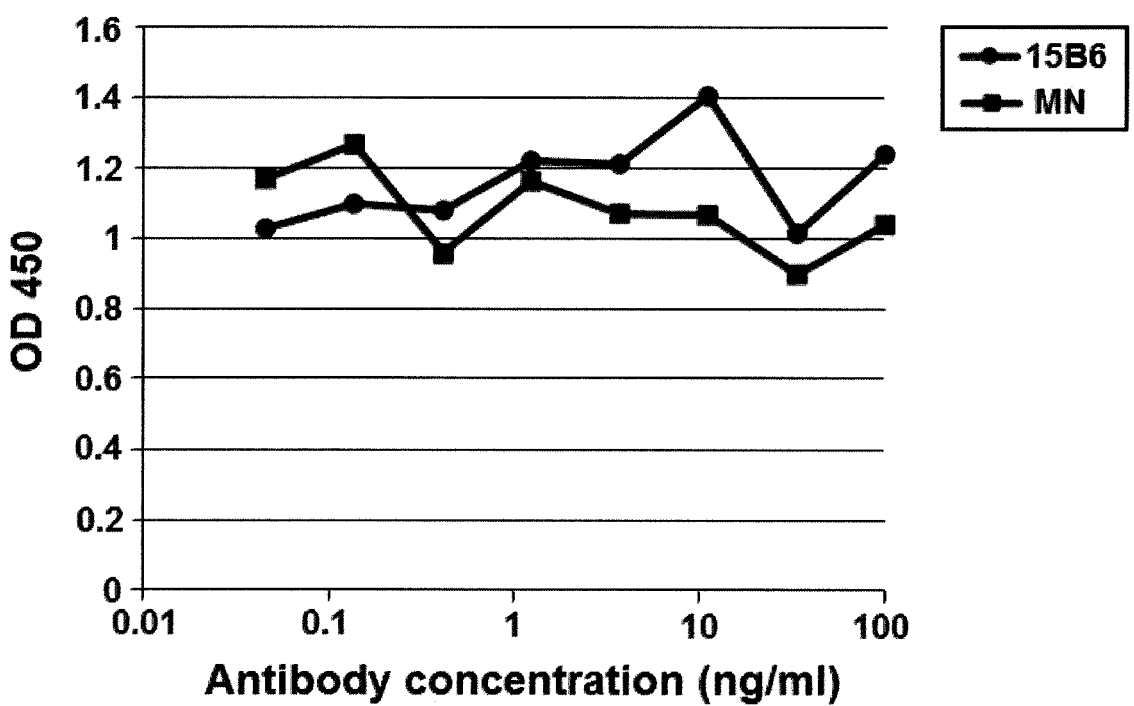
FIG. 18 is a graph showing growth inhibition of RH29 cells, attributable to 15B6 (comprising SEQ ID NOs: 14-19) (circles) or control antibody MN (squares) at the indicated concentrations, measured by a WST-8 cell proliferation assay kit. 15B6 antibody did not affect the growth of RH29 cells.

RH29 cells were treated with 15B6 antibodies of Example 1 at concentrations ranging from less than 0.1 to 100 ug/ml to determine if they would inhibit growth of these cells. MN was used as the control antibody. The number of viable cells after 72 hours was measured by a WST-8 cell proliferation assay kit. The WST-8 proliferation assay (OD 450) results are shown in FIG. 18. These results indicate that no RH29 cell growth inhibition by 15B6 was observed under these in vitro conditions.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

---

The invention claimed is:

1. A polypeptide comprising an antigen binding domain of an antibody, the antigen binding domain comprising:
   (i) the heavy chain complementarity determining region (CDR) 1 amino acid sequence of SEQ ID NO: 2,
   the heavy chain CDR2 amino acid sequence of SEQ ID NO: 3,
   the heavy chain CDR3 amino acid sequence of SEQ ID NO: 4,
   the light chain CDR1 amino acid sequence of SEQ ID NO: 5,
   the light chain CDR2 amino acid sequence of SEQ ID NO: 6, and
   the light chain CDR3 amino acid sequence of SEQ ID NO: 7;
   (ii) the heavy chain CDR1 amino acid sequence of SEQ ID NO: 8,
   the heavy chain CDR2 amino acid sequence of SEQ ID NO: 9,
   the heavy chain CDR3 amino acid sequence of SEQ ID NO: 10,
   the light chain CDR1 amino acid sequence of SEQ ID NO: 11,
   the light chain CDR2 amino acid sequence of SEQ ID NO: 12, and the light chain CDR3 amino acid sequence of SEQ ID NO: 13; or (iii) the heavy chain CDR1 amino acid sequence of SEQ ID NO: 14,
the heavy chain CDR2 amino acid sequence of SEQ ID NO: 15,
the heavy chain CDR3 amino acid sequence of SEQ ID NO: 16,
the light chain CDR1 amino acid sequence of SEQ ID NO: 17,
the light chain CDR2 amino acid sequence of SEQ ID NO: 18, and
the light chain CDR3 amino acid sequence of SEQ ID NO: 19;

wherein the antigen binding domain comprises a heavy chain variable region and a light chain variable region, and specifically recognizes and binds to human mesothelin$_{582-598}$ (IPNGYLVLDLSMQEALS) (SEQ ID NO: 1).

2. The polypeptide of claim 1, wherein the antigen binding domain comprises the amino acid sequences of (i) SEQ ID NOs: 20 and 21, (ii) SEQ ID NOs: 22 and 23, or (iii) SEQ ID NOs: 24 and 25.

3. A conjugate comprising (a) the polypeptide of claim 1, conjugated or fused to (b) an effector molecule, wherein the effector molecule is a drug, toxin, label, small molecule, or an antibody.

4. The conjugate according to claim 3, wherein the effector molecule is Pseudomonas exotoxin A (PE) or a variant thereof.

5. The conjugate of claim 3, wherein the effector molecule is a drug.

6. The polypeptide of claim 1, wherein the polypeptide is single-chain variable region fragment (scFv) or disulfide-stabilized variable region fragment (dsFv).

7. A pharmaceutical composition comprising the polypeptide of claim 1 and a pharmaceutically acceptable carrier.

8. A kit for treating cancer, the kit comprising the polypeptide of claim 1.

9. A nucleic acid comprising a nucleotide sequence encoding the polypeptide of claim 1.

10. The nucleic acid according to claim 9, comprising a nucleotide sequence comprising (i) SEQ ID NOs: 26 and 27, (ii) SEQ ID NOs: 28 and 29, or (iii) SEQ ID NOs: 30 and 31.

11. A recombinant expression vector comprising the nucleic acid of claim 9.

12. An isolated host cell comprising the recombinant expression vector of claim 11.

13. A population of isolated cells comprising at least one host cell of claim 12.

14. A method of detecting the presence of cancer in a mammal, the method comprising:
(a) contacting a sample comprising one or more cells from the mammal with the polypeptide of claim 1, thereby forming a complex, and
(b) detecting the complex, wherein detection of the complex is indicative of the presence of cancer.

15. A method of treating cancer in a mammal, the method comprising administering to the mammal the polypeptide of claim 1 in an amount effective to treat cancer in the mammal.

16. An antibody, or an antigen binding portion of an antibody, comprising:
(i) the heavy chain complementarity determining region (CDR) 1 amino acid sequence of SEQ ID NO: 2,
the heavy chain CDR2 amino acid sequence of SEQ ID NO: 3,
the heavy chain CDR3 amino acid sequence of SEQ ID NO: 4,
the light chain CDR1 amino acid sequence of SEQ ID NO: 5,
the light chain CDR2 amino acid sequence of SEQ ID NO: 6, and
the light chain CDR3 amino acid sequence of SEQ ID NO: 7;
(ii) the heavy chain CDR1 amino acid sequence of SEQ ID NO: 8,
the heavy chain CDR2 amino acid sequence of SEQ ID NO: 9,
the heavy chain CDR3 amino acid sequence of SEQ ID NO: 10,
the light chain CDR1 amino acid sequence of SEQ ID NO: 11,
the light chain CDR2 amino acid sequence of SEQ ID NO: 12, and
the light chain CDR3 amino acid sequence of SEQ ID NO: 13; or
(iii) the heavy chain CDR1 amino acid sequence of SEQ ID NO: 14,
the heavy chain CDR2 amino acid sequence of SEQ ID NO: 15,
the heavy chain CDR3 amino acid sequence of SEQ ID NO: 16,
the light chain CDR1 amino acid sequence of SEQ ID NO: 17,
the light chain CDR2 amino acid sequence of SEQ ID NO: 18, and
the light chain CDR3 amino acid sequence of SEQ ID NO: 19;
wherein the antibody and the antigen binding portion of the antibody specifically recognize and bind to human mesothelin$_{582-598}$ (IPNGYLVLDLSMQEALS) (SEQ ID NO: 1).

17. The antibody, or the antigen binding portion of the antibody, of claim 16 comprising:
(a) the amino acid sequences of SEQ ID NO: 20 and SEQ ID NO: 21;
(b) the amino acid sequences of SEQ ID NO: 22 and SEQ ID NO: 23; or
(c) the amino acid sequences of SEQ ID NO: 24 and SEQ ID NO: 25.

18. The antibody, or the antigen binding portion of the antibody, of claim 16, wherein the antibody, or the antigen binding portion of the antibody is a Fab fragment (Fab), F(ab')$_2$ fragment, diabody, triabody, tetrabody, or bispecific antibody.

19. The antibody of claim 16, wherein the antibody is a bispecific antibody.

\* \* \* \* \*

SEQUENCE LISTING

```
<160> NUMBER OF SEQ ID NOS: 64

<210> SEQ ID NO 1
<211> LENGTH: 17
<212> TYPE: PRT
<213> ORGANISM: Homo sapiens

<400> SEQUENCE: 1

Ile Pro Asn Gly Tyr Leu Val Leu Asp Leu Ser Met Gln Glu Ala Leu
1               5                   10                  15

Ser

<210> SEQ ID NO 2
<211> LENGTH: 5
<212> TYPE: PRT
<213> ORGANISM: Mus musculus

<400> SEQUENCE: 2

Gly His Tyr Met His
1               5

<210> SEQ ID NO 3
<211> LENGTH: 17
<212> TYPE: PRT
<213> ORGANISM: Mus musculus

<400> SEQUENCE: 3

Arg Ile Asn Pro Tyr Thr Gly Ala Ile Asn Tyr Asn Gln Asn Phe Lys
1               5                   10                  15
```

Asp

<210> SEQ ID NO 4
<211> LENGTH: 6
<212> TYPE: PRT
<213> ORGANISM: Mus musculus

<400> SEQUENCE: 4

Asp Leu Gly Gly Gly Tyr
1               5

<210> SEQ ID NO 5
<211> LENGTH: 14
<212> TYPE: PRT
<213> ORGANISM: Mus musculus

<400> SEQUENCE: 5

Arg Ser Ser Thr Gly Ala Val Thr Thr Ser Asn Tyr Ala Asn
1               5                   10

<210> SEQ ID NO 6
<211> LENGTH: 7
<212> TYPE: PRT
<213> ORGANISM: Mus musculus

<400> SEQUENCE: 6

Gly Thr Asn Asn Arg Ala Pro
1               5

<210> SEQ ID NO 7
<211> LENGTH: 9
<212> TYPE: PRT
<213> ORGANISM: Mus musculus

<400> SEQUENCE: 7

Ala Leu Trp Tyr Ser Ser His Trp Val
1               5

<210> SEQ ID NO 8
<211> LENGTH: 5
<212> TYPE: PRT
<213> ORGANISM: Mus musculus

<400> SEQUENCE: 8

Gly His Tyr Met His
1               5

<210> SEQ ID NO 9
<211> LENGTH: 17
<212> TYPE: PRT
<213> ORGANISM: Mus musculus

<400> SEQUENCE: 9

Arg Ile Asn Pro Tyr Thr Gly Ala Ile Asn Tyr Asn Gln Asn Phe Lys
1               5                   10                  15
Asp

<210> SEQ ID NO 10
<211> LENGTH: 6
<212> TYPE: PRT
<213> ORGANISM: Mus musculus

<400> SEQUENCE: 10

Asp Leu Gly Gly Gly Tyr
1               5

<210> SEQ ID NO 11
<211> LENGTH: 14
<212> TYPE: PRT
<213> ORGANISM: Mus musculus

<400> SEQUENCE: 11

Arg Ser Ser Thr Gly Ala Val Thr Thr Ser Asn Tyr Ala Asn
1               5                   10

<210> SEQ ID NO 12
<211> LENGTH: 7
<212> TYPE: PRT
<213> ORGANISM: Mus musculus

<400> SEQUENCE: 12

Gly Thr Asn Asn Arg Ala Pro
1               5

<210> SEQ ID NO 13
<211> LENGTH: 9
<212> TYPE: PRT
<213> ORGANISM: Mus musculus

<400> SEQUENCE: 13

Ala Leu Trp Phe Gly Ser His Trp Val
1               5

<210> SEQ ID NO 14
<211> LENGTH: 5
<212> TYPE: PRT
<213> ORGANISM: Mus musculus

<400> SEQUENCE: 14

Gly Tyr Tyr Met His
1               5

<210> SEQ ID NO 15
<211> LENGTH: 17
<212> TYPE: PRT
<213> ORGANISM: Mus musculus

<400> SEQUENCE: 15

Arg Ile Asn Pro Tyr Thr Gly Val Pro Ser Tyr Lys His Asn Phe Lys
1               5                   10                  15

Asp

<210> SEQ ID NO 16
<211> LENGTH: 5
<212> TYPE: PRT
<213> ORGANISM: Mus musculus

<400> SEQUENCE: 16

Glu Leu Gly Gly Tyr
1               5

<210> SEQ ID NO 17
<211> LENGTH: 14
<212> TYPE: PRT
<213> ORGANISM: Mus musculus

<400> SEQUENCE: 17

Arg Ser Ser Thr Gly Ala Val Thr Gly Asn Tyr Pro Asn
1               5                   10

<210> SEQ ID NO 18
<211> LENGTH: 7
<212> TYPE: PRT
<213> ORGANISM: Mus musculus

<400> SEQUENCE: 18

Gly Thr Asn Asn Arg Ala Pro
1               5

<210> SEQ ID NO 19
<211> LENGTH: 9
<212> TYPE: PRT
<213> ORGANISM: Mus musculus

<400> SEQUENCE: 19

Ala Leu Trp Phe Ser Ser His Trp Val
1               5

<210> SEQ ID NO 20
<211> LENGTH: 115
<212> TYPE: PRT
<213> ORGANISM: Mus musculus

<400> SEQUENCE: 20

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Pro Phe Thr Gly His
                20                  25                  30

Tyr Met His Trp Val Lys Gln Gly His Val Lys Ser Leu Glu Trp Ile
            35                  40                  45

Gly Arg Ile Asn Pro Tyr Thr Gly Ala Ile Asn Tyr Asn Gln Asn Phe
        50                  55                  60

Lys Asp Lys Ala Ser Leu Ser Val Glu Lys Ser Ser Thr Ala Tyr
65                  70                  75                  80

Met Gly Leu His Ser Leu Thr Ser Glu Asp Ser Ala Val Tyr Tyr Cys
                85                  90                  95

Val Arg Asp Leu Gly Gly Gly Tyr Trp Gly Gln Gly Thr Thr Leu Thr
            100                 105                 110

Val Ser Ser
        115

<210> SEQ ID NO 21
<211> LENGTH: 109
<212> TYPE: PRT
<213> ORGANISM: Mus musculus

<400> SEQUENCE: 21

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
                20                  25                  30

Asn Tyr Ala Asn Trp Val Gln Glu Lys Pro Asp His Leu Phe Thr Gly
            35                  40                  45

Leu Ile Ala Gly Thr Asn Asn Arg Ala Pro Gly Val Pro Ala Arg Phe
        50                  55                  60

Ser Gly Ser Leu Ile Gly Asp Lys Ala Ala Leu Thr Ile Thr Gly Ala
65                  70                  75                  80

```
Gln Pro Glu Asp Glu Ala Ile Phe Phe Cys Ala Leu Trp Tyr Ser Ser
                85                  90                  95

His Trp Val Phe Gly Gly Gly Thr Lys Leu Thr Val Leu
            100                 105

<210> SEQ ID NO 22
<211> LENGTH: 115
<212> TYPE: PRT
<213> ORGANISM: Mus musculus

<400> SEQUENCE: 22

Glu Val Gln Leu Gln Gln Ser Gly Pro Glu Leu Val Lys Pro Gly Thr
1               5                   10                  15

Ser Val Lys Ile Ser Cys Lys Ala Ser Gly Tyr Pro Phe Thr Gly His
                20                  25                  30

Tyr Met His Trp Val Lys Gln Gly His Val Lys Ser Leu Glu Trp Ile
            35                  40                  45

Gly Arg Ile Asn Pro Tyr Thr Gly Ala Ile Asn Tyr Asn Gln Asn Phe
        50                  55                  60

Lys Asp Lys Ala Ser Leu Thr Val Glu Lys Ser Ser Ser Thr Ala Tyr
65                  70                  75                  80

Met Gly Leu His Ser Leu Thr Ser Glu Asp Ser Ala Val Tyr Tyr Cys
                85                  90                  95

Val Arg Asp Leu Gly Gly Tyr Trp Gly Gln Gly Thr Thr Leu Thr
            100                 105                 110

Val Ser Ser
        115

<210> SEQ ID NO 23
<211> LENGTH: 109
<212> TYPE: PRT
<213> ORGANISM: Mus musculus

<400> SEQUENCE: 23

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
                20                  25                  30

Asn Tyr Ala Asn Trp Val Gln Glu Lys Pro Asp His Leu Phe Thr Gly
            35                  40                  45

Leu Ile Ala Gly Thr Asn Asn Arg Ala Pro Gly Val Pro Ala Arg Phe
        50                  55                  60

Ser Gly Ser Leu Ile Gly Asp Lys Ala Ala Leu Thr Ile Thr Gly Ala
65                  70                  75                  80

Gln Pro Glu Asp Glu Ala Met Phe Phe Cys Ala Leu Trp Phe Gly Ser
                85                  90                  95

His Trp Val Phe Gly Gly Gly Thr Lys Leu Thr Val Leu
            100                 105

<210> SEQ ID NO 24
<211> LENGTH: 114
<212> TYPE: PRT
<213> ORGANISM: Mus musculus

<400> SEQUENCE: 24

Glu Val Gln Leu Gln Gln Ser Gly Pro Val Leu Val Lys Pro Gly Ala
1               5                   10                  15
```

Ser Val Lys Ile Ser Cys Lys Ala Ser Gly Tyr Ser Phe Thr Gly Tyr
            20                  25                  30

Tyr Met His Trp Val Arg Gln Ser Leu Val Lys Arg Leu Glu Trp Ile
        35                  40                  45

Gly Arg Ile Asn Pro Tyr Thr Gly Val Pro Ser Tyr Lys His Asn Phe
    50                  55                  60

Lys Asp Lys Ala Ser Leu Thr Val Asp Lys Ser Ser Thr Ala Tyr
65                  70                  75                  80

Met Glu Leu His Ser Leu Thr Ser Glu Asp Ser Ala Val Tyr Tyr Cys
                85                  90                  95

Ala Arg Glu Leu Gly Gly Tyr Trp Gly Gln Gly Thr Thr Leu Thr Val
            100                 105                 110

Ser Ser

<210> SEQ ID NO 25
<211> LENGTH: 109
<212> TYPE: PRT
<213> ORGANISM: Mus musculus

<400> SEQUENCE: 25

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Gly
            20                  25                  30

Asn Tyr Pro Asn Trp Val Gln Glu Lys Pro Asp His Leu Phe Thr Gly
        35                  40                  45

Leu Ile Ala Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Phe Ser Ser
                85                  90                  95

His Trp Val Phe Gly Gly Gly Thr Lys Leu Thr Val Leu
            100                 105

<210> SEQ ID NO 26
<211> LENGTH: 345
<212> TYPE: DNA
<213> ORGANISM: Mus musculus

<400> SEQUENCE: 26
gaggtccagc tgcaacagtc tggacctgag ctggtgaagc ctggggcttc agtgaagata     60
tcctgcaagg cttctggtta cccattcact ggccactaca tgcactgggt gaagcaaggc    120
catgtaaaga gccttgagtg gattggacga attaatcctt acactggtgc tattaactac    180
aaccagaatt tcaaggacaa ggccagcttg agtgtagaga gtcctccag tacagcctac    240 atgggcctcc acagcctgac atctgaggac tctgcagtct attactgtgt gagagactta    300
ggagggggct actggggcca aggcaccact ctcacagtct cctca                    345

<210> SEQ ID NO 27
<211> LENGTH: 327
<212> TYPE: DNA
<213> ORGANISM: Mus musculus

<400> SEQUENCE: 27
caggctgttg tgactcagga atctgcactc accacatcac ctggtgaaac agtcacactc     60

| | |
|---|---|
| acttgtcgct caagtactgg ggctgttaca actagtaact atgccaactg ggtccaagaa | 120 |
| aaaccagatc atttattcac tggtctaata gctggtacca acaaccgagc tccaggtgtt | 180 |
| cctgccagat tctcaggctc cctgattgga gacaaggctg ccctcaccat cacaggggca | 240 |
| cagcctgagg atgaggcaat atttttctgt gctctatggt acagcagcca ttgggtgttc | 300 |
| ggtggaggaa ccaaactgac tgtccta | 327 |

<210> SEQ ID NO 28
<211> LENGTH: 345
<212> TYPE: DNA
<213> ORGANISM: Mus musculus

<400> SEQUENCE: 28

| | |
|---|---|
| gaggtccagc tgcaacagtc tggacctgag ctggtgaagc ctgggacttc agtgaagata | 60 |
| tcctgcaagg cttctggtta ccctttcact ggccactaca tgcactgggt gaagcaaggc | 120 |
| catgtcaaga gccttgagtg gattggacga attaatcctt acactggtgc tattaactac | 180 |
| aaccagaatt tcaaggacaa ggccagcttg actgtagaga agtcctccag tacagcctat | 240 |
| atgggcctcc atagtctgac atctgaggac tctgcagtct attactgtgt gagagactta | 300 |
| ggaggggggct actggggcca aggcaccact ctcacagtct cctca | 345 |

<210> SEQ ID NO 29
<211> LENGTH: 327
<212> TYPE: DNA
<213> ORGANISM: Mus musculus

<400> SEQUENCE: 29

| | |
|---|---|
| caggctgttg tgactcagga atctgcactc accacatcac ctggtgaaac agtcacactc | 60 |
| acttgtcgct caagtactgg ggctgtcaca actagtaact atgccaactg ggtccaagaa | 120 |
| aaaccagatc atttattcac tggtctaata gctggtacca acaaccgagc tccaggtgtt | 180 |
| cctgccagat tctcaggctc cctgattgga gacaaggctg ccctcaccat cacaggggct | 240 |
| cagcctgagg atgaggcaat gttttttctgt gctctttggt tcggcagcca ttgggtgttc | 300 |
| ggtggaggaa ccaaactgac tgtcctg | 327 |

<210> SEQ ID NO 30
<211> LENGTH: 342
<212> TYPE: DNA
<213> ORGANISM: Mus musculus

<400> SEQUENCE: 30

| | |
|---|---|
| gaggtccagc tgcaacagtc tggacctgta ctggtgaagc ctggggcttc agtgaagata | 60 |
| tcctgcaagg cttctggtta ctcattcact ggctactaca tgcactgggt gaggcaaagc | 120 |
| cttgtaaaga gacttgagtg gattggacgt attaatcctt acactggtgt tccttcctac | 180 |
| aagcataatt tcaaggacaa ggccagcttg actgtagata agtcctccag cacagcctac | 240 |
| atggagctcc acagcctgac ctctgaggac tctgcagtct attactgtgc aagagaactg | 300 |
| ggaggctact ggggccaagg caccactctc acagtctcct ca | 342 |

<210> SEQ ID NO 31
<211> LENGTH: 327
<212> TYPE: DNA
<213> ORGANISM: Mus musculus

<400> SEQUENCE: 31

| | |
|---|---|
| caggctgttg tgactcagga atctgcactc accacatcac ctggtgaaac agtcacactc | 60 |

-continued

```
acttgtcgct caagtactgg ggctgttaca actggtaact atcccaactg ggtccaagaa    120
aaaccagatc atttattcac tggtctaata gctggtacca acaaccgagc tccaggtgtt    180
cctgccagat tctcaggctc cctgattgga gacaaggctg ccctcaccat cacaggggca    240
cagactgagg atgaggcaat atatttctgt gctctatggt tcagcagcca ttgggtgttc    300
ggtggaggaa ccaagctgac tgtcctc                                        327
```

<210> SEQ ID NO 32
<211> LENGTH: 30
<212> TYPE: PRT
<213> ORGANISM: Mus musculus

<400> SEQUENCE: 32

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Pro Phe Thr
            20                  25                  30

<210> SEQ ID NO 33
<211> LENGTH: 14
<212> TYPE: PRT
<213> ORGANISM: Mus musculus

<400> SEQUENCE: 33

Trp Val Lys Gln Gly His Val Lys Ser Leu Glu Trp Ile Gly
1               5                   10

<210> SEQ ID NO 34
<211> LENGTH: 32
<212> TYPE: PRT
<213> ORGANISM: Mus musculus

<400> SEQUENCE: 34

Lys Ala Ser Leu Ser Val Glu Lys Ser Ser Thr Ala Tyr Met Gly
1               5                   10                  15

Leu His Ser Leu Thr Ser Glu Asp Ser Ala Val Tyr Tyr Cys Val Arg
            20                  25                  30

<210> SEQ ID NO 35
<211> LENGTH: 11
<212> TYPE: PRT
<213> ORGANISM: Mus musculus

<400> SEQUENCE: 35

Trp Gly Gln Gly Thr Thr Leu Thr Val Ser Ser
1               5                   10

<210> SEQ ID NO 36
<211> LENGTH: 22
<212> TYPE: PRT
<213> ORGANISM: Mus musculus

<400> SEQUENCE: 36

Gln Ala Val Val Thr Gln Glu Ser Ala Leu Thr Thr Ser Pro Gly Glu
1               5                   10                  15

Thr Val Thr Leu Thr Cys
            20

<210> SEQ ID NO 37
<211> LENGTH: 15
<212> TYPE: PRT

<213> ORGANISM: Mus musculus

<400> SEQUENCE: 37

Trp Val Gln Glu Lys Pro Asp His Leu Phe Thr Gly Leu Ile Ala
1               5                   10                  15

<210> SEQ ID NO 38
<211> LENGTH: 32
<212> TYPE: PRT
<213> ORGANISM: Mus musculus

<400> SEQUENCE: 38

Gly Val Pro Ala Arg Phe Ser Gly Ser Leu Ile Gly Asp Lys Ala Ala
1               5                   10                  15

Leu Thr Ile Thr Gly Ala Gln Pro Glu Asp Glu Ala Ile Phe Phe Cys
                20                  25                  30

<210> SEQ ID NO 39
<211> LENGTH: 10
<212> TYPE: PRT
<213> ORGANISM: Mus musculus

<400> SEQUENCE: 39

Phe Gly Gly Gly Thr Lys Leu Thr Val Leu
1               5                   10

<210> SEQ ID NO 40
<211> LENGTH: 30
<212> TYPE: PRT
<213> ORGANISM: Mus musculus

<400> SEQUENCE: 40

Glu Val Gln Leu Gln Gln Ser Gly Pro Glu Leu Val Lys Pro Gly Thr
1               5                   10                  15

Ser Val Lys Ile Ser Cys Lys Ala Ser Gly Tyr Pro Phe Thr
                20                  25                  30

<210> SEQ ID NO 41
<211> LENGTH: 14
<212> TYPE: PRT
<213> ORGANISM: Mus musculus

<400> SEQUENCE: 41

Trp Val Lys Gln Gly His Val Lys Ser Leu Glu Trp Ile Gly
1               5                   10

<210> SEQ ID NO 42
<211> LENGTH: 32
<212> TYPE: PRT
<213> ORGANISM: Mus musculus

<400> SEQUENCE: 42

Lys Ala Ser Leu Thr Val Glu Lys Ser Ser Thr Ala Tyr Met Gly
1               5                   10                  15

Leu His Ser Leu Thr Ser Glu Asp Ser Ala Val Tyr Tyr Cys Val Arg
                20                  25                  30

<210> SEQ ID NO 43
<211> LENGTH: 11
<212> TYPE: PRT
<213> ORGANISM: Mus musculus

<400> SEQUENCE: 43

Trp Gly Gln Gly Thr Thr Leu Thr Val Ser Ser
1               5                   10

<210> SEQ ID NO 44
<211> LENGTH: 22
<212> TYPE: PRT
<213> ORGANISM: Mus musculus

<400> SEQUENCE: 44

Gln Ala Val Val Thr Gln Glu Ser Ala Leu Thr Thr Ser Pro Gly Glu
1               5                   10                  15

Thr Val Thr Leu Thr Cys
            20

<210> SEQ ID NO 45
<211> LENGTH: 15
<212> TYPE: PRT
<213> ORGANISM: Mus musculus

<400> SEQUENCE: 45

Trp Val Gln Glu Lys Pro Asp His Leu Phe Thr Gly Leu Ile Ala
1               5                   10                  15

<210> SEQ ID NO 46
<211> LENGTH: 32
<212> TYPE: PRT
<213> ORGANISM: Mus musculus

<400> SEQUENCE: 46

Gly Val Pro Ala Arg Phe Ser Gly Ser Leu Ile Gly Asp Lys Ala Ala
1               5                   10                  15

Leu Thr Ile Thr Gly Ala Gln Pro Glu Asp Glu Ala Met Phe Phe Cys
            20                  25                  30

<210> SEQ ID NO 47
<211> LENGTH: 10
<212> TYPE: PRT
<213> ORGANISM: Mus musculus

<400> SEQUENCE: 47

Phe Gly Gly Gly Thr Lys Leu Thr Val Leu
1               5                   10

<210> SEQ ID NO 48
<211> LENGTH: 30
<212> TYPE: PRT
<213> ORGANISM: Mus musculus

<400> SEQUENCE: 48

Glu Val Gln Leu Gln Gln Ser Gly Pro Val Leu Val Lys Pro Gly Ala
1               5                   10                  15

Ser Val Lys Ile Ser Cys Lys Ala Ser Gly Tyr Ser Phe Thr
            20                  25                  30

<210> SEQ ID NO 49
<211> LENGTH: 14
<212> TYPE: PRT
<213> ORGANISM: Mus musculus

<400> SEQUENCE: 49

Trp Val Arg Gln Ser Leu Val Lys Arg Leu Glu Trp Ile Gly
1               5                   10

```
<210> SEQ ID NO 50
<211> LENGTH: 32
<212> TYPE: PRT
<213> ORGANISM: Mus musculus

<400> SEQUENCE: 50

Lys Ala Ser Leu Thr Val Asp Lys Ser Ser Thr Ala Tyr Met Glu
1               5                   10                  15

Leu His Ser Leu Thr Ser Glu Asp Ser Ala Val Tyr Tyr Cys Ala Arg
            20                  25                  30

<210> SEQ ID NO 51
<211> LENGTH: 11
<212> TYPE: PRT
<213> ORGANISM: Mus musculus

<400> SEQUENCE: 51

Trp Gly Gln Gly Thr Thr Leu Thr Val Ser Ser
1               5                   10

<210> SEQ ID NO 52
<211> LENGTH: 22
<212> TYPE: PRT
<213> ORGANISM: Mus musculus

<400> SEQUENCE: 52

Gln Ala Val Val Thr Gln Glu Ser Ala Leu Thr Thr Ser Pro Gly Glu
1               5                   10                  15

Thr Val Thr Leu Thr Cys
            20

<210> SEQ ID NO 53
<211> LENGTH: 15
<212> TYPE: PRT
<213> ORGANISM: Mus musculus

<400> SEQUENCE: 53

Trp Val Gln Glu Lys Pro Asp His Leu Phe Thr Gly Leu Ile Ala
1               5                   10                  15

<210> SEQ ID NO 54
<211> LENGTH: 32
<212> TYPE: PRT
<213> ORGANISM: Mus musculus

<400> SEQUENCE: 54

Gly Val Pro Ala Arg Phe Ser Gly Ser Leu Ile Gly Asp Lys Ala Ala
1               5                   10                  15

Leu Thr Ile Thr Gly Ala Gln Thr Glu Asp Glu Ala Ile Tyr Phe Cys
            20                  25                  30

<210> SEQ ID NO 55
<211> LENGTH: 10
<212> TYPE: PRT
<213> ORGANISM: Mus musculus

<400> SEQUENCE: 55

Phe Gly Gly Gly Thr Lys Leu Thr Val Leu
1               5                   10

<210> SEQ ID NO 56
<211> LENGTH: 622
<212> TYPE: PRT
<213> ORGANISM: Homo sapiens
```

<400> SEQUENCE: 56

```
Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
            20                  25                  30

Pro Ser Arg Thr Leu Ala Gly Glu Thr Gly Gln Glu Ala Ala Pro Leu
        35                  40                  45

Asp Gly Val Leu Ala Asn Pro Asn Ile Ser Ser Leu Ser Pro Arg
    50                  55                  60

Gln Leu Leu Gly Phe Pro Cys Ala Glu Val Ser Gly Leu Ser Thr Glu
65                  70                  75                  80

Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
            100                 105                 110

Glu Asp Leu Asp Ala Leu Pro Leu Asp Leu Leu Leu Phe Leu Asn Pro
        115                 120                 125

Asp Ala Phe Ser Gly Pro Gln Ala Cys Thr Arg Phe Phe Ser Arg Ile
130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Gln Glu Ala Ala Arg
210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
            260                 265                 270

Gln Arg Ser Ser Arg Asp Pro Ser Trp Arg Gln Pro Glu Arg Thr Ile
        275                 280                 285

Leu Arg Pro Arg Phe Arg Arg Glu Val Glu Lys Thr Ala Cys Pro Ser
290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
            340                 345                 350

Lys His Lys Leu Asp Glu Leu Tyr Pro Gln Gly Tyr Pro Glu Ser Val
        355                 360                 365

Ile Gln His Leu Gly Tyr Leu Phe Leu Lys Met Ser Pro Glu Asp Ile
370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Val Ala Thr Leu Ile Asp
```

-continued

```
                405                 410                 415
Arg Phe Val Lys Gly Arg Gly Gln Leu Asp Lys Asp Thr Leu Asp Thr
            420                 425                 430

Leu Thr Ala Phe Tyr Pro Gly Tyr Leu Cys Ser Leu Ser Pro Glu Glu
        435                 440                 445

Leu Ser Ser Val Pro Pro Ser Ser Ile Trp Ala Val Arg Pro Gln Asp
    450                 455                 460

Leu Asp Thr Cys Asp Pro Arg Gln Leu Asp Val Leu Tyr Pro Lys Ala
465                 470                 475                 480

Arg Leu Ala Phe Gln Asn Met Asn Gly Ser Glu Tyr Phe Val Lys Ile
                485                 490                 495

Gln Ser Phe Leu Gly Gly Ala Pro Thr Glu Asp Leu Lys Ala Leu Ser
            500                 505                 510

Gln Gln Asn Val Ser Met Asp Leu Ala Thr Phe Met Lys Leu Arg Thr
        515                 520                 525

Asp Ala Val Leu Pro Leu Thr Val Ala Glu Val Gln Lys Leu Leu Gly
    530                 535                 540

Pro His Val Glu Gly Leu Lys Ala Glu Arg His Arg Pro Val Arg
545                 550                 555                 560

Asp Trp Ile Leu Arg Gln Arg Gln Asp Asp Leu Asp Thr Leu Gly Leu
                565                 570                 575

Gly Leu Gln Gly Gly Ile Pro Asn Gly Tyr Leu Val Leu Asp Leu Ser
            580                 585                 590

Met Gln Glu Ala Leu Ser Gly Thr Pro Cys Leu Leu Gly Pro Gly Pro
        595                 600                 605

Val Leu Thr Val Leu Ala Leu Leu Ala Ser Thr Leu Ala
    610                 615                 620
```

<210> SEQ ID NO 57
<211> LENGTH: 21
<212> TYPE: PRT
<213> ORGANISM: Homo sapiens

<400> SEQUENCE: 57

```
Gln Arg Gln Asp Asp Leu Asp Thr Leu Gly Leu Gly Leu Gln Gly Gly
1               5                   10                  15

Ile Pro Asn Gly Tyr
            20
```

<210> SEQ ID NO 58
<211> LENGTH: 12
<212> TYPE: PRT
<213> ORGANISM: Homo sapiens

<400> SEQUENCE: 58

```
Leu Val Leu Asp Leu Ser Met Gln Glu Ala Leu Ser
1               5                   10
```

<210> SEQ ID NO 59
<211> LENGTH: 26
<212> TYPE: PRT
<213> ORGANISM: Homo sapiens

<400> SEQUENCE: 59

```
Gln Arg Gln Asp Asp Leu Asp Thr Leu Gly Leu Gly Leu Gln Gly Gly
1               5                   10                  15

Ile Pro Asn Gly Tyr Leu Val Leu Asp Leu
            20                  25
```

```
<210> SEQ ID NO 60
<211> LENGTH: 7
<212> TYPE: PRT
<213> ORGANISM: Homo sapiens

<400> SEQUENCE: 60

Ser Met Gln Glu Ala Leu Ser
1               5

<210> SEQ ID NO 61
<211> LENGTH: 13
<212> TYPE: PRT
<213> ORGANISM: Artificial Sequence
<220> FEATURE:
<223> OTHER INFORMATION: Synthetic

<400> SEQUENCE: 61

Cys Leu Val Leu Asp Leu Ser Met Gln Glu Ala Leu Ser
1               5                   10

<210> SEQ ID NO 62
<211> LENGTH: 8
<212> TYPE: PRT
<213> ORGANISM: Artificial Sequence
<220> FEATURE:
<223> OTHER INFORMATION: Synthetic

<400> SEQUENCE: 62

Cys Ser Met Gln Glu Ala Leu Ser
1               5

<210> SEQ ID NO 63
<211> LENGTH: 5
<212> TYPE: PRT
<213> ORGANISM: Homo sapiens

<400> SEQUENCE: 63

Leu Val Leu Asp Leu
1               5

<210> SEQ ID NO 64
<211> LENGTH: 24
<212> TYPE: PRT
<213> ORGANISM: Mus musculus

<400> SEQUENCE: 64

Leu Cys Phe Ala Ala Ile Ala Leu Val Ile Phe Phe Leu Ile Gly Phe
1               5                   10                  15

Met Ser Gly Tyr Leu Gly Tyr Gly
            20
```